US012385045B2

(12) United States Patent
Lokhov et al.

(10) Patent No.: US 12,385,045 B2
(45) Date of Patent: *Aug. 12, 2025

(54) THERMOSTABLE POLYMERASE INHIBITOR COMPOSITIONS AND METHODS

(71) Applicant: Cepheid, Sunnyvale, CA (US)

(72) Inventors: Sergey G. Lokhov, Seattle, WA (US); Alexander A. Gall, Woodinville, WA (US); Vera Baraznenok, Sunnyvale, CA (US); Ekaterina V. Viazovkina, Sunnyvale, CA (US); Irina Shishkina, Sunnyvale, CA (US); David H. Persing, San Martin, CA (US)

(73) Assignee: Cepheid, Sunnyvale, CA (US)

( * ) Notice: Subject to any disclaimer, the term of this patent is extended or adjusted under 35 U.S.C. 154(b) by 228 days.

This patent is subject to a terminal disclaimer.

(21) Appl. No.: 17/687,473

(22) Filed: Mar. 4, 2022

(65) Prior Publication Data

US 2022/0389427 A1 Dec. 8, 2022

Related U.S. Application Data

(63) Continuation of application No. 16/305,858, filed as application No. PCT/US2017/036225 on Jun. 6, 2017, now Pat. No. 11,299,739.

(60) Provisional application No. 62/347,004, filed on Jun. 7, 2016.

(51) Int. Cl.
C12N 15/115 (2010.01)
C12Q 1/6853 (2018.01)
C12Q 1/686 (2018.01)

(52) U.S. Cl.
CPC .......... C12N 15/115 (2013.01); C12Q 1/6853 (2013.01); C12Q 1/686 (2013.01); *C12N 2310/16* (2013.01); *C12N 2310/531* (2013.01); *C12N 2310/532* (2013.01); *C12N 2320/52* (2013.01); *C12Q 2525/205* (2013.01)

(58) Field of Classification Search
CPC .............. C12Q 1/6853; C12Q 1/686; C12Q 2525/205; C12N 15/115; C12N 2310/16; C12N 2310/531; C12N 2310/532; C12N 2320/52
See application file for complete search history.

(56) References Cited

U.S. PATENT DOCUMENTS

| | | |
|---|---|---|
| 5,874,557 A | 2/1999 | Gold et al. |
| 6,183,967 B1 | 2/2001 | Jayasena et al. |
| 6,667,165 B2 | 12/2003 | Peters |
| 8,313,932 B2 | 11/2012 | Moser et al. |
| 8,530,194 B2 | 9/2013 | Mao et al. |
| 10,689,629 B1 | 6/2020 | Kutyavin et al. |
| 10,724,017 B1 | 7/2020 | Kutyavin et al. |
| 10,724,083 B1 | 7/2020 | Kutyavin et al. |
| 11,155,859 B2 | 10/2021 | Kutyavin et al. |
| 11,299,739 B2 | 4/2022 | Lokhov et al. |
| 2001/0053519 A1* | 12/2001 | Fodor ............. G03F 7/265 536/24.1 |
| 2015/0176059 A1 | 6/2015 | Fiss et al. |
| 2019/0316132 A1 | 10/2019 | Lokhov et al. |
| 2020/0392471 A1 | 12/2020 | Kutyavin et al. |
| 2020/0392561 A1 | 12/2020 | Kutyavin et al. |

FOREIGN PATENT DOCUMENTS

| | | | |
|---|---|---|---|
| JP | 2016540517 A | 12/2016 | |
| WO | WO-0052207 A1 | 9/2000 | |
| WO | WO-2006086669 A2 | 8/2006 | |
| WO | WO-2007041201 A2 * | 4/2007 | ........... C12N 15/115 |
| WO | WO-2015091720 A1 | 6/2015 | |
| WO | WO-2016072758 A1 | 5/2016 | |
| WO | WO-2017214202 A1 | 12/2017 | |

OTHER PUBLICATIONS

Chou et al. (1992) "Prevention of pre-PCR mis-priming and primer dimerization improves low-copy-number amplifications" Nucleic Acids Research 20(7): 1717-1723.
Dorjsuren et al. (2009) "A real-time fluorescence method for enzymatic characterization of specialized human DNA polymerases" Nucleic Acids Research 37(19): e128 (12 pages).
Giusto, D. and King, G.C. "Construction, Stability, and Activity of Multivalent Circular Anticoagulant Aptamers", The Journal of Biological Chemistry, 2004, vol. 279, No. 45, pp. 46463-46489.
Lin, Y. and Jayasena, S.D. "Inhibition of Multiple Thermostable DNA Polymerases by a Heterodimeric Aptamer", 1997, Journal of Molecular Biology, vol. 271, pp. 100-111.
Ma et al. (2006) "Real-time monitoring of DNA polymerase activity using molecular beacon" Analytical Biochemistry 353: 141-143.
Nikiforov (2011) "Fluorogenic polymerase, endonuclease, and ligase assays based on DNA substrates labeled with a single fluorophore" Analytical Biochemistry 412: 229-236.
Nikiforov (2012) "Fluorogenic substrates with single fluorophores for nucleic acid-modifying enzymes: Design principles and new applications" Analytical Biochemistry 424: 142-148.
Notice of Allowance dated Dec. 2, 2021 in U.S. Appl. No. 16/305,858.
Summerer and Marx (2002) "A Molecular Beacon for Quantitative Monitoring of the DNA Polymerase Reaction in Real-Time" Angewandte Chemie International Edition 41(19): 3620-3622.
Yakimovich, O.Y. et al., "Influence of DNA Aptamer Structure on the Specificity of Binding to Taq DNA Polymerase" Biochemistry, 2003, vol. 68, No. 2, pp. 228-235.

* cited by examiner

*Primary Examiner* — Cynthia B Wilder
*Assistant Examiner* — Kailey Elizabeth Cash
(74) *Attorney, Agent, or Firm* — McAndrews, Held & Malloy, Ltd.

(57) ABSTRACT

The present disclosure relates to aptamers for temperature-dependent reversible inhibition of thermostable polymerase activity in order to improve sensitivity and specificity of various reactions and assays involving hot start polynucleotide synthesis. Methods for use of the aptamers and related compositions and kits are also provided.

20 Claims, 7 Drawing Sheets

Specification includes a Sequence Listing.

```
       TTTGC G
  ATATTAACGTTTTATT   A
A TTCTT                TTCTT
G CGTTT TATAATTGCAAAATAA TTCTT
```
(SEQ ID NO:110)

FIG. 1A

5'-CAATTTATATATTCTTAGCGTTTTTATAATTGCAAAATAAATTCTTAGCGTTTTTATTTTG-3'
(SEQ ID NO:110)

FIG. 1B

```
                                  TTTGC G
3'-CGATTCTTAATAAAAATTTTAATAT      A  (SEQ ID NO:90)
   5'-GTTTTTATTTTAAAAATTATA   TTCTT
```

FIG. 3A

5'-GTTTTTATTTTAAAAATTATATTCTTAGCGTTTTATTTTAAAATAAATTCTTAGC-3' (SEQ ID NO:90)

FIG. 3B

SEQUENCE LISTING

```
<160> NUMBER OF SEQ ID NOS: 111

<210> SEQ ID NO 1
<211> LENGTH: 16
<212> TYPE: DNA
<213> ORGANISM: Artificial
<220> FEATURE:
<223> OTHER INFORMATION: Synthetic

<400> SEQUENCE: 1
tataattgca aaataa                                                     16

<210> SEQ ID NO 2
<211> LENGTH: 16
<212> TYPE: DNA
<213> ORGANISM: Artificial
<220> FEATURE:
<223> OTHER INFORMATION: Synthetic

<400> SEQUENCE: 2
ttattttgca attata                                                     16

<210> SEQ ID NO 3
<211> LENGTH: 12
<212> TYPE: DNA
<213> ORGANISM: Artificial
<220> FEATURE:
<223> OTHER INFORMATION: Synthetic
```

<400> SEQUENCE: 3
ttcttagcgt tt                                                          12

<210> SEQ ID NO 4
<211> LENGTH: 16
<212> TYPE: DNA
<213> ORGANISM: Artificial
<220> FEATURE:
<223> OTHER INFORMATION: Synthetic

<400> SEQUENCE: 4 tataattta aaataa                                                       16

<210> SEQ ID NO 5
<211> LENGTH: 16
<212> TYPE: DNA
<213> ORGANISM: Artificial
<220> FEATURE:
<223> OTHER INFORMATION: Synthetic

<400> SEQUENCE: 5 ttatttaaa attata                                                       16

<210> SEQ ID NO 6
<211> LENGTH: 40
<212> TYPE: DNA
<213> ORGANISM: Artificial
<220> FEATURE:
<223> OTHER INFORMATION: Synthetic
<220> FEATURE:
<221> NAME/KEY: modified_base
<222> LOCATION: (38)..(38)
<223> OTHER INFORMATION: n is a fluorescein dT residue

<400> SEQUENCE: 6 ttttttttgca ggtgacaggc gcgaagcgcc tgtcaccngc                            40

<210> SEQ ID NO 7
<211> LENGTH: 29
<212> TYPE: DNA
<213> ORGANISM: Artificial
<220> FEATURE:
<223> OTHER INFORMATION: Synthetic

<400> SEQUENCE: 7
aaaaggcatt cctgaagctg acagcattc                                        29

<210> SEQ ID NO 8
<211> LENGTH: 24
<212> TYPE: DNA
<213> ORGANISM: Artificial
<220> FEATURE:
<223> OTHER INFORMATION: Synthetic

<400> SEQUENCE: 8
gagagagtag cgcgagcaca gcta                                             24

<210> SEQ ID NO 9
<211> LENGTH: 26
<212> TYPE: DNA
<213> ORGANISM: Artificial
<220> FEATURE:
<223> OTHER INFORMATION: Synthetic

<400> SEQUENCE: 9
aaaacctgcc ttctgcgtga gattct                                           26

```
<210> SEQ ID NO 10
<211> LENGTH: 26
<212> TYPE: DNA
<213> ORGANISM: Artificial
<220> FEATURE:
<223> OTHER INFORMATION: Synthetic

<400> SEQUENCE: 10
ctgtacgaaa agaccacagg gcccat                                          26

<210> SEQ ID NO 11
<211> LENGTH: 16
<212> TYPE: DNA
<213> ORGANISM: Artificial
<220> FEATURE:
<223> OTHER INFORMATION: Synthetic

<400> SEQUENCE: 11
atattaaaaa attata                                                     16

<210> SEQ ID NO 12
<211> LENGTH: 16
<212> TYPE: DNA
<213> ORGANISM: Artificial
<220> FEATURE:
<223> OTHER INFORMATION: Synthetic

<400> SEQUENCE: 12
tataattttt taatat                                                     16

<210> SEQ ID NO 13
<211> LENGTH: 14
<212> TYPE: DNA
<213> ORGANISM: Artificial
<220> FEATURE:
<223> OTHER INFORMATION: Synthetic

<400> SEQUENCE: 13
atattaaaat tata                                                       14

<210> SEQ ID NO 14
<211> LENGTH: 14
<212> TYPE: DNA
<213> ORGANISM: Artificial
<220> FEATURE:
<223> OTHER INFORMATION: Synthetic

<400> SEQUENCE: 14
tataatttta atat                                                       14

<210> SEQ ID NO 15
<211> LENGTH: 16
<212> TYPE: DNA
<213> ORGANISM: Artificial
<220> FEATURE:
<223> OTHER INFORMATION: Synthetic

<400> SEQUENCE: 15
atattaaaaa attata                                                     16

<210> SEQ ID NO 16
<211> LENGTH: 16
<212> TYPE: DNA
<213> ORGANISM: Artificial
<220> FEATURE:
```

<223> OTHER INFORMATION: Synthetic

<400> SEQUENCE: 16
tataattttt taatat                                                        16

<210> SEQ ID NO 17
<211> LENGTH: 16
<212> TYPE: DNA
<213> ORGANISM: Artificial
<220> FEATURE:
<223> OTHER INFORMATION: Synthetic

<400> SEQUENCE: 17
ttattttaaa attata                                                        16

<210> SEQ ID NO 18
<211> LENGTH: 16
<212> TYPE: DNA
<213> ORGANISM: Artificial
<220> FEATURE:
<223> OTHER INFORMATION: Synthetic

<400> SEQUENCE: 18
tataatttta aaataa                                                        16

<210> SEQ ID NO 19
<211> LENGTH: 16
<212> TYPE: DNA
<213> ORGANISM: Artificial
<220> FEATURE:
<223> OTHER INFORMATION: Synthetic

<400> SEQUENCE: 19
ttattttaaa attata                                                        16

<210> SEQ ID NO 20
<211> LENGTH: 16
<212> TYPE: DNA
<213> ORGANISM: Artificial
<220> FEATURE:
<223> OTHER INFORMATION: Synthetic

<400> SEQUENCE: 20
tataattcca aaataa                                                        16

<210> SEQ ID NO 21
<211> LENGTH: 16
<212> TYPE: DNA
<213> ORGANISM: Artificial
<220> FEATURE:
<223> OTHER INFORMATION: Synthetic

<400> SEQUENCE: 21
ttattttgga attata                                                        16

<210> SEQ ID NO 22
<211> LENGTH: 16
<212> TYPE: DNA
<213> ORGANISM: Artificial
<220> FEATURE:
<223> OTHER INFORMATION: Synthetic

<400> SEQUENCE: 22
tataattgca aaataa                                                        16

```
<210> SEQ ID NO 23
<211> LENGTH: 16
<212> TYPE: DNA
<213> ORGANISM: Artificial
<220> FEATURE:
<223> OTHER INFORMATION: Synthetic

<400> SEQUENCE: 23
ttattttgca attata                                                   16

<210> SEQ ID NO 24
<211> LENGTH: 16
<212> TYPE: DNA
<213> ORGANISM: Artificial
<220> FEATURE:
<223> OTHER INFORMATION: Synthetic

<400> SEQUENCE: 24
tataattcga aaataa                                                   16

<210> SEQ ID NO 25
<211> LENGTH: 16
<212> TYPE: DNA
<213> ORGANISM: Artificial
<220> FEATURE:
<223> OTHER INFORMATION: Synthetic

<400> SEQUENCE: 25
ttattttcga attata                                                   16

<210> SEQ ID NO 26
<211> LENGTH: 16
<212> TYPE: DNA
<213> ORGANISM: Artificial
<220> FEATURE:
<223> OTHER INFORMATION: Synthetic

<400> SEQUENCE: 26
ttattttaaa attata                                                   16

<210> SEQ ID NO 27
<211> LENGTH: 16
<212> TYPE: DNA
<213> ORGANISM: Artificial
<220> FEATURE:
<223> OTHER INFORMATION: Synthetic

<400> SEQUENCE: 27
tataatttta aaataa                                                   16

<210> SEQ ID NO 28
<211> LENGTH: 16
<212> TYPE: DNA
<213> ORGANISM: Artificial
<220> FEATURE:
<223> OTHER INFORMATION: Synthetic

<400> SEQUENCE: 28
ttattttcca attata                                                   16

<210> SEQ ID NO 29
<211> LENGTH: 16
<212> TYPE: DNA
<213> ORGANISM: Artificial
<220> FEATURE:
<223> OTHER INFORMATION: Synthetic
```

<400> SEQUENCE: 29
tataattgga aaataa                                                    16

<210> SEQ ID NO 30
<211> LENGTH: 16
<212> TYPE: DNA
<213> ORGANISM: Artificial
<220> FEATURE:
<223> OTHER INFORMATION: Synthetic

<400> SEQUENCE: 30
ttattttgca attata                                                    16

<210> SEQ ID NO 31
<211> LENGTH: 16
<212> TYPE: DNA
<213> ORGANISM: Artificial
<220> FEATURE:
<223> OTHER INFORMATION: Synthetic

<400> SEQUENCE: 31
tataattgca aaataa                                                    16

<210> SEQ ID NO 32
<211> LENGTH: 16
<212> TYPE: DNA
<213> ORGANISM: Artificial
<220> FEATURE:
<223> OTHER INFORMATION: Synthetic

<400> SEQUENCE: 32
ttattttcga attata                                                    16

<210> SEQ ID NO 33
<211> LENGTH: 16
<212> TYPE: DNA
<213> ORGANISM: Artificial
<220> FEATURE:
<223> OTHER INFORMATION: Synthetic

<400> SEQUENCE: 33
tataattcga aaataa                                                    16

<210> SEQ ID NO 34
<211> LENGTH: 14
<212> TYPE: DNA
<213> ORGANISM: Artificial
<220> FEATURE:
<223> OTHER INFORMATION: Synthetic

<400> SEQUENCE: 34
tattttaaaa atat                                                      14

<210> SEQ ID NO 35
<211> LENGTH: 14
<212> TYPE: DNA
<213> ORGANISM: Artificial
<220> FEATURE:
<223> OTHER INFORMATION: Synthetic

<400> SEQUENCE: 35
atatttttaa aata                                                      14

<210> SEQ ID NO 36
<211> LENGTH: 14

```
<212> TYPE: DNA
<213> ORGANISM: Artificial
<220> FEATURE:
<223> OTHER INFORMATION: Synthetic

<400> SEQUENCE: 36 tattttaaa atat                                                       14

<210> SEQ ID NO 37
<211> LENGTH: 14
<212> TYPE: DNA
<213> ORGANISM: Artificial
<220> FEATURE:
<223> OTHER INFORMATION: Synthetic

<400> SEQUENCE: 37
atattttaaa aata                                                      14

<210> SEQ ID NO 38
<211> LENGTH: 14
<212> TYPE: DNA
<213> ORGANISM: Artificial
<220> FEATURE:
<223> OTHER INFORMATION: Synthetic

<400> SEQUENCE: 38
tattttaaaa atat                                                      14

<210> SEQ ID NO 39
<211> LENGTH: 15
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (8)..(8)
<223> OTHER INFORMATION: n is a DMT-ethane-diol phosphoroamidite (C-2
      spacer)

<400> SEQUENCE: 39
atattttnta aaata                                                     15

<210> SEQ ID NO 40
<211> LENGTH: 14
<212> TYPE: DNA
<213> ORGANISM: Artificial
<220> FEATURE:
<223> OTHER INFORMATION: Synthetic

<400> SEQUENCE: 40 tattttaaa atat                                                       14

<210> SEQ ID NO 41
<211> LENGTH: 15
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (8)..(8)
<223> OTHER INFORMATION: n is a DMT-ethane-diol phosphoroamidite (C-2
      spacer)

<400> SEQUENCE: 41
atattttnaa aaata                                                     15
```

<210> SEQ ID NO 42
<211> LENGTH: 56
<212> TYPE: DNA
<213> ORGANISM: Artificial
<220> FEATURE:
<223> OTHER INFORMATION: Synthetic

<400> SEQUENCE: 42
caaaataatt cttagcgttt ttattttgca attatattct tagcgtttta taattg    56

<210> SEQ ID NO 43
<211> LENGTH: 56
<212> TYPE: DNA
<213> ORGANISM: Artificial
<220> FEATURE:
<223> OTHER INFORMATION: Synthetic

<400> SEQUENCE: 43
caattatatt cttagcgttt tataattgca aaataattct tagcgttttt attttg    56

<210> SEQ ID NO 44
<211> LENGTH: 56
<212> TYPE: DNA
<213> ORGANISM: Artificial
<220> FEATURE:
<223> OTHER INFORMATION: Synthetic

<400> SEQUENCE: 44
taaaataatt cttagcgttt ttattttaaa attatattct tagcgtttta taattt    56

<210> SEQ ID NO 45
<211> LENGTH: 56
<212> TYPE: DNA
<213> ORGANISM: Artificial
<220> FEATURE:
<223> OTHER INFORMATION: Synthetic

<400> SEQUENCE: 45
caaaataatt cttagcgttt ttattttgga attatattct tagcgtttta taattc    56

<210> SEQ ID NO 46
<211> LENGTH: 56
<212> TYPE: DNA
<213> ORGANISM: Artificial
<220> FEATURE:
<223> OTHER INFORMATION: Synthetic

<400> SEQUENCE: 46
gaaaataatt cttagcgttt ttattttcga attatattct tagcgtttta taattc    56

<210> SEQ ID NO 47
<211> LENGTH: 56
<212> TYPE: DNA
<213> ORGANISM: Artificial
<220> FEATURE:
<223> OTHER INFORMATION: Synthetic

<400> SEQUENCE: 47
aaattatatt cttagcgttt tataatttta aaataattct tagcgttttt atttta    56

<210> SEQ ID NO 48
<211> LENGTH: 56
<212> TYPE: DNA
<213> ORGANISM: Artificial
<220> FEATURE:
<223> OTHER INFORMATION: Synthetic

<400> SEQUENCE: 48
caattatatt cttagcgttt tataattgga aaataattct tagcgttttt attttc        56

<210> SEQ ID NO 49
<211> LENGTH: 56
<212> TYPE: DNA
<213> ORGANISM: Artificial
<220> FEATURE:
<223> OTHER INFORMATION: Synthetic

<400> SEQUENCE: 49
gaattatatt cttagcgttt tataattcga aaataattct tagcgttttt attttc        56

<210> SEQ ID NO 50
<211> LENGTH: 52
<212> TYPE: DNA
<213> ORGANISM: Artificial
<220> FEATURE:
<223> OTHER INFORMATION: Synthetic

<400> SEQUENCE: 50
aaaatatttc ttagcgttta tattttaaaa atattcttag cgttttattt ta            52

<210> SEQ ID NO 51
<211> LENGTH: 52
<212> TYPE: DNA
<213> ORGANISM: Artificial
<220> FEATURE:
<223> OTHER INFORMATION: Synthetic

<400> SEQUENCE: 51
aaaatatttc ttagcgttta tattttaaaa atattcttag cgttttattt tt            52

<210> SEQ ID NO 52
<211> LENGTH: 53
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (27)..(27)
<223> OTHER INFORMATION: n is a DMT-ethane-diol phosphoroamidite (C-2
      spacer)

<400> SEQUENCE: 52
aaaatatttc ttagcgttta tattttntaa aatattctta gcgttttatt tta           53

<210> SEQ ID NO 53
<211> LENGTH: 53
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (27)..(27)
<223> OTHER INFORMATION: n is a DMT-ethane-diol phosphoroamidite (C-2
      spacer)

<400> SEQUENCE: 53
aaaatatttc ttagcgttta tattttnaaa atattctta gcgttttatt ttt            53

<210> SEQ ID NO 54
<211> LENGTH: 54
<212> TYPE: DNA

```
<213> ORGANISM: Artificial
<220> FEATURE:
<223> OTHER INFORMATION: Synthetic

<400> SEQUENCE: 54
aaattatatc ttagcgtttt ataattttttt aatattctta gcgtttatat taaa        54

<210> SEQ ID NO 55
<211> LENGTH: 50
<212> TYPE: DNA
<213> ORGANISM: Artificial
<220> FEATURE:
<223> OTHER INFORMATION: Synthetic

<400> SEQUENCE: 55
aattatatct tagcgtttta taattttaat attcttagcg tttatattaa              50

<210> SEQ ID NO 56
<211> LENGTH: 56
<212> TYPE: DNA
<213> ORGANISM: Artificial
<220> FEATURE:
<223> OTHER INFORMATION: Synthetic

<400> SEQUENCE: 56
aaattatatt cttagcgttt tataatttttt taatatttct tagcgtttat attaaa      56

<210> SEQ ID NO 57
<211> LENGTH: 56
<212> TYPE: DNA
<213> ORGANISM: Artificial
<220> FEATURE:
<223> OTHER INFORMATION: Synthetic

<400> SEQUENCE: 57
aaattatatt cttagcgttt tataatttta aataattct tagcgttttt atttta        56

<210> SEQ ID NO 58
<211> LENGTH: 16
<212> TYPE: DNA
<213> ORGANISM: Artificial
<220> FEATURE:
<223> OTHER INFORMATION: Synthetic

<400> SEQUENCE: 58 ttatttttaaa attata                                                  16

<210> SEQ ID NO 59
<211> LENGTH: 16
<212> TYPE: DNA
<213> ORGANISM: Artificial
<220> FEATURE:
<223> OTHER INFORMATION: Synthetic

<400> SEQUENCE: 59
tataatttta aaataa                                                   16

<210> SEQ ID NO 60
<211> LENGTH: 16
<212> TYPE: DNA
<213> ORGANISM: Artificial
<220> FEATURE:
<223> OTHER INFORMATION: Synthetic

<400> SEQUENCE: 60
tatttttaaa aatata                                                   16
```

```
<210> SEQ ID NO 61
<211> LENGTH: 16
<212> TYPE: DNA
<213> ORGANISM: Artificial
<220> FEATURE:
<223> OTHER INFORMATION: Synthetic

<400> SEQUENCE: 61 tatatttta aaaata                                                       16

<210> SEQ ID NO 62
<211> LENGTH: 16
<212> TYPE: DNA
<213> ORGANISM: Artificial
<220> FEATURE:
<223> OTHER INFORMATION: Synthetic

<400> SEQUENCE: 62
ttaatttaaa tttata                                                      16

<210> SEQ ID NO 63
<211> LENGTH: 16
<212> TYPE: DNA
<213> ORGANISM: Artificial
<220> FEATURE:
<223> OTHER INFORMATION: Synthetic

<400> SEQUENCE: 63
tataaattta aattaa                                                      16

<210> SEQ ID NO 64
<211> LENGTH: 16
<212> TYPE: DNA
<213> ORGANISM: Artificial
<220> FEATURE:
<223> OTHER INFORMATION: Synthetic

<400> SEQUENCE: 64
ttaattttaa aatata                                                      16

<210> SEQ ID NO 65
<211> LENGTH: 16
<212> TYPE: DNA
<213> ORGANISM: Artificial
<220> FEATURE:
<223> OTHER INFORMATION: Synthetic

<400> SEQUENCE: 65
tatattttaa aattaa                                                      16

<210> SEQ ID NO 66
<211> LENGTH: 16
<212> TYPE: DNA
<213> ORGANISM: Artificial
<220> FEATURE:
<223> OTHER INFORMATION: Synthetic

<400> SEQUENCE: 66 ttattttaa aaaata                                                       16

<210> SEQ ID NO 67
<211> LENGTH: 16
<212> TYPE: DNA
<213> ORGANISM: Artificial
<220> FEATURE:
```

```
<223> OTHER INFORMATION: Synthetic

<400> SEQUENCE: 67
tattttttaa aaataa                                                      16

<210> SEQ ID NO 68
<211> LENGTH: 16
<212> TYPE: DNA
<213> ORGANISM: Artificial
<220> FEATURE:
<223> OTHER INFORMATION: Synthetic

<400> SEQUENCE: 68
ttatatttaa attata                                                      16

<210> SEQ ID NO 69
<211> LENGTH: 16
<212> TYPE: DNA
<213> ORGANISM: Artificial
<220> FEATURE:
<223> OTHER INFORMATION: Synthetic

<400> SEQUENCE: 69
tataatttaa atataa                                                      16

<210> SEQ ID NO 70
<211> LENGTH: 14
<212> TYPE: DNA
<213> ORGANISM: Artificial
<220> FEATURE:
<223> OTHER INFORMATION: Synthetic

<400> SEQUENCE: 70
tatattttta aaaa                                                        14

<210> SEQ ID NO 71
<211> LENGTH: 16
<212> TYPE: DNA
<213> ORGANISM: Artificial
<220> FEATURE:
<223> OTHER INFORMATION: Synthetic

<400> SEQUENCE: 71 taattttta aaaatat                                                      16

<210> SEQ ID NO 72
<211> LENGTH: 15
<212> TYPE: DNA
<213> ORGANISM: Artificial
<220> FEATURE:
<223> OTHER INFORMATION: Synthetic

<400> SEQUENCE: 72 taatttaaa aaata                                                        15

<210> SEQ ID NO 73
<211> LENGTH: 15
<212> TYPE: DNA
<213> ORGANISM: Artificial
<220> FEATURE:
<223> OTHER INFORMATION: Synthetic

<400> SEQUENCE: 73
tattttttaa aatta                                                       15
```

```
<210> SEQ ID NO 74
<211> LENGTH: 15
<212> TYPE: DNA
<213> ORGANISM: Artificial
<220> FEATURE:
<223> OTHER INFORMATION: Synthetic

<400> SEQUENCE: 74
ttatttttaa aaaat                                                     15

<210> SEQ ID NO 75
<211> LENGTH: 15
<212> TYPE: DNA
<213> ORGANISM: Artificial
<220> FEATURE:
<223> OTHER INFORMATION: Synthetic

<400> SEQUENCE: 75 atttttttaaa aataa                                                    15

<210> SEQ ID NO 76
<211> LENGTH: 14
<212> TYPE: DNA
<213> ORGANISM: Artificial
<220> FEATURE:
<223> OTHER INFORMATION: Synthetic

<400> SEQUENCE: 76
taattttaaa aaat                                                      14

<210> SEQ ID NO 77
<211> LENGTH: 14
<212> TYPE: DNA
<213> ORGANISM: Artificial
<220> FEATURE:
<223> OTHER INFORMATION: Synthetic

<400> SEQUENCE: 77
attttttaaa atta                                                      14

<210> SEQ ID NO 78
<211> LENGTH: 13
<212> TYPE: DNA
<213> ORGANISM: Artificial
<220> FEATURE:
<223> OTHER INFORMATION: Synthetic

<400> SEQUENCE: 78
taattttaaa aat                                                       13

<210> SEQ ID NO 79
<211> LENGTH: 13
<212> TYPE: DNA
<213> ORGANISM: Artificial
<220> FEATURE:
<223> OTHER INFORMATION: Synthetic

<400> SEQUENCE: 79
atttttaaaa tta                                                       13

<210> SEQ ID NO 80
<211> LENGTH: 13
<212> TYPE: DNA
<213> ORGANISM: Artificial
<220> FEATURE:
<223> OTHER INFORMATION: Synthetic
```

<400> SEQUENCE: 80
caattttaaa aat                                                          13

<210> SEQ ID NO 81
<211> LENGTH: 13
<212> TYPE: DNA
<213> ORGANISM: Artificial
<220> FEATURE:
<223> OTHER INFORMATION: Synthetic

<400> SEQUENCE: 81 attttttaaaa ttg                                                         13

<210> SEQ ID NO 82
<211> LENGTH: 56
<212> TYPE: DNA
<213> ORGANISM: Artificial
<220> FEATURE:
<223> OTHER INFORMATION: Synthetic

<400> SEQUENCE: 82
gcgtttttat ttaaaatta tattcttagc gttttataat tttaaaataa ttctta            56

<210> SEQ ID NO 83
<211> LENGTH: 56
<212> TYPE: DNA
<213> ORGANISM: Artificial
<220> FEATURE:
<223> OTHER INFORMATION: Synthetic

<400> SEQUENCE: 83
ttattttaaa attatattct tagcgtttta taattttaaa ataattctta gcgttt           56

<210> SEQ ID NO 84
<211> LENGTH: 56
<212> TYPE: DNA
<213> ORGANISM: Artificial
<220> FEATURE:
<223> OTHER INFORMATION: Synthetic

<400> SEQUENCE: 84
ttcttagcgt ttttatttta aaattatatt cttagcgttt tataatttta aaataa           56

<210> SEQ ID NO 85
<211> LENGTH: 56
<212> TYPE: DNA
<213> ORGANISM: Artificial
<220> FEATURE:
<223> OTHER INFORMATION: Synthetic

<400> SEQUENCE: 85
gcgttttata atttttaaaat aattcttagc gttttttattt taaaattata ttctta         56

<210> SEQ ID NO 86
<211> LENGTH: 56
<212> TYPE: DNA
<213> ORGANISM: Artificial
<220> FEATURE:
<223> OTHER INFORMATION: Synthetic

<400> SEQUENCE: 86
ttcttagcgt tttataaattt taaaataatt cttagcgttt ttatttttaaa attata         56

<210> SEQ ID NO 87
<211> LENGTH: 56

```
<212> TYPE: DNA
<213> ORGANISM: Artificial
<220> FEATURE:
<223> OTHER INFORMATION: Synthetic

<400> SEQUENCE: 87 tataattttta aaataattct tagcgttttt attttaaaat tatattctta gcgttt        56

<210> SEQ ID NO 88
<211> LENGTH: 56
<212> TYPE: DNA
<213> ORGANISM: Artificial
<220> FEATURE:
<223> OTHER INFORMATION: Synthetic

<400> SEQUENCE: 88
cgtttttatt ttaaaattat attcttagcg ttttataatt ttaaaataat tcttag        56

<210> SEQ ID NO 89
<211> LENGTH: 56
<212> TYPE: DNA
<213> ORGANISM: Artificial
<220> FEATURE:
<223> OTHER INFORMATION: Synthetic

<400> SEQUENCE: 89
agcgttttta ttttaaaatt atattcttag cgttttataa ttttaaaata attctt        56

<210> SEQ ID NO 90
<211> LENGTH: 56
<212> TYPE: DNA
<213> ORGANISM: Artificial
<220> FEATURE:
<223> OTHER INFORMATION: Synthetic

<400> SEQUENCE: 90
gtttttattt taaaattata ttcttagcgt tttataattt taaaataatt cttagc        56

<210> SEQ ID NO 91
<211> LENGTH: 56
<212> TYPE: DNA
<213> ORGANISM: Artificial
<220> FEATURE:
<223> OTHER INFORMATION: Synthetic

<400> SEQUENCE: 91
tagcgttttt attttaaaat tatattctta gcgttttata attttaaaat aattct        56

<210> SEQ ID NO 92
<211> LENGTH: 56
<212> TYPE: DNA
<213> ORGANISM: Artificial
<220> FEATURE:
<223> OTHER INFORMATION: Synthetic

<400> SEQUENCE: 92
gcgttttatt tttaaaaata tattcttagc gtttatatt tttaaaaata ttctta         56

<210> SEQ ID NO 93
<211> LENGTH: 56
<212> TYPE: DNA
<213> ORGANISM: Artificial
<220> FEATURE:
<223> OTHER INFORMATION: Synthetic

<400> SEQUENCE: 93
```
gcgtttttaa tttaaattta tattcttagc gttttataaa tttaaattaa ttctta      56

<210> SEQ ID NO 94
<211> LENGTH: 56
<212> TYPE: DNA
<213> ORGANISM: Artificial
<220> FEATURE:
<223> OTHER INFORMATION: Synthetic

<400> SEQUENCE: 94
gcgtttttaa ttttaaaata tattcttagc gttttatatt ttaaaattaa ttctta      56

<210> SEQ ID NO 95
<211> LENGTH: 56
<212> TYPE: DNA
<213> ORGANISM: Artificial
<220> FEATURE:
<223> OTHER INFORMATION: Synthetic

<400> SEQUENCE: 95
gcgtttttat ttttaaaaaa tattcttagc gttttatttt ttaaaaataa ttctta      56

<210> SEQ ID NO 96
<211> LENGTH: 56
<212> TYPE: DNA
<213> ORGANISM: Artificial
<220> FEATURE:
<223> OTHER INFORMATION: Synthetic

<400> SEQUENCE: 96
gcgtttttat atttaaatta tattcttagc gttttataat ttaaatataa ttctta      56

<210> SEQ ID NO 97
<211> LENGTH: 56
<212> TYPE: DNA
<213> ORGANISM: Artificial
<220> FEATURE:
<223> OTHER INFORMATION: Synthetic

<400> SEQUENCE: 97
cgtttttatt tttaaaaaat attcttagcg ttttattttt taaaaataat tcttag      56

<210> SEQ ID NO 98
<211> LENGTH: 56
<212> TYPE: DNA
<213> ORGANISM: Artificial
<220> FEATURE:
<223> OTHER INFORMATION: Synthetic

<400> SEQUENCE: 98 gttttattt ttaaaaaata ttcttagcgt tttatttttt aaaataatt cttagc      56

<210> SEQ ID NO 99
<211> LENGTH: 56
<212> TYPE: DNA
<213> ORGANISM: Artificial
<220> FEATURE:
<223> OTHER INFORMATION: Synthetic

<400> SEQUENCE: 99
cgtttatatt tttaaaaatt attcttagcg ttttaatttt taaaaatatt tcttag      56

<210> SEQ ID NO 100
<211> LENGTH: 56
<212> TYPE: DNA
<213> ORGANISM: Artificial

<220> FEATURE:
<223> OTHER INFORMATION: Synthetic

<400> SEQUENCE: 100 gtttatatttt taaaaatta ttcttagcgt tttaattttt aaaatatttt cttagc    56

<210> SEQ ID NO 101
<211> LENGTH: 54
<212> TYPE: DNA
<213> ORGANISM: Artificial
<220> FEATURE:
<223> OTHER INFORMATION: Synthetic

<400> SEQUENCE: 101
gttttaattt taaaaatat tcttagcgtt ttatttttta aaattattct tagc    54

<210> SEQ ID NO 102
<211> LENGTH: 54
<212> TYPE: DNA
<213> ORGANISM: Artificial
<220> FEATURE:
<223> OTHER INFORMATION: Synthetic

<400> SEQUENCE: 102
gtttttattt taaaaaatt tcttagcgtt tattttttaa aaataattct tagc    54

<210> SEQ ID NO 103
<211> LENGTH: 52
<212> TYPE: DNA
<213> ORGANISM: Artificial
<220> FEATURE:
<223> OTHER INFORMATION: Synthetic

<400> SEQUENCE: 103
gttttaattt taaaaaattt cttagcgttt attttttaaa attattctta gc    52

<210> SEQ ID NO 104
<211> LENGTH: 50
<212> TYPE: DNA
<213> ORGANISM: Artificial
<220> FEATURE:
<223> OTHER INFORMATION: Synthetic

<400> SEQUENCE: 104
gttttaattt taaaaatttc ttagcgttta tttttaaaat tattcttagc    50

<210> SEQ ID NO 105
<211> LENGTH: 50
<212> TYPE: DNA
<213> ORGANISM: Artificial
<220> FEATURE:
<223> OTHER INFORMATION: Synthetic

<400> SEQUENCE: 105
gtttcaattt taaaaatttc ttagcgttta tttttaaaat tgttcttagc    50

<210> SEQ ID NO 106
<211> LENGTH: 56
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (56)..(56)
<223> OTHER INFORMATION: g is linked to a propanediol spacer (C3)

<400> SEQUENCE: 106
caaaataatt cttagcgttt ttattttgca attatattct tagcgtttta taattg    56

<210> SEQ ID NO 107
<211> LENGTH: 56
<212> TYPE: DNA
<213> ORGANISM: Artificial
<220> FEATURE:
<223> OTHER INFORMATION: Synthetic
<220> FEATURE:
<223> OTHER INFORMATION: Synthetic
<220> FEATURE:
<221> NAME/KEY: misc_feature
<222> LOCATION: (56)..(56)
<223> OTHER INFORMATION: c is linked to a propanediol spacer (C3)

<400> SEQUENCE: 107
caaaataatt cttagcgttt ttattttgga attatattct tagcgtttta taattc    56

<210> SEQ ID NO 108
<211> LENGTH: 56
<212> TYPE: DNA
<213> ORGANISM: Artificial
<220> FEATURE:
<223> OTHER INFORMATION: Synthetic
<220> FEATURE:
<223> OTHER INFORMATION: Synthetic
<220> FEATURE:
<221> NAME/KEY: misc_feature
<222> LOCATION: (56)..(56)
<223> OTHER INFORMATION: c is linked to a propanediol spacer (C3)

<400> SEQUENCE: 108
gaaaataatt cttagcgttt ttattttcga attatattct tagcgtttta taattc    56

<210> SEQ ID NO 109
<211> LENGTH: 56
<212> TYPE: DNA
<213> ORGANISM: Artificial
<220> FEATURE:
<223> OTHER INFORMATION: Synthetic
<220> FEATURE:
<223> OTHER INFORMATION: Synthetic
<220> FEATURE:
<221> NAME/KEY: misc_feature
<222> LOCATION: (56)..(56)
<223> OTHER INFORMATION: c is linked to a propanediol spacer (C3)

<400> SEQUENCE: 109
caattatatt cttagcgttt tataattgga aaataattct tagcgttttt attttc    56

<210> SEQ ID NO 110
<211> LENGTH: 56
<212> TYPE: DNA
<213> ORGANISM: Artificial
<220> FEATURE:
<223> OTHER INFORMATION: Synthetic
<220> FEATURE:
<223> OTHER INFORMATION: Synthetic
<220> FEATURE:
<221> NAME/KEY: misc_feature
<222> LOCATION: (56)..(56)
<223> OTHER INFORMATION: g is linked to a propanediol spacer (C3)

<400> SEQUENCE: 110
caattatatt cttagcgttt tataattgca aaataattct tagcgttttt attttg    56

<210> SEQ ID NO 111
<211> LENGTH: 56

```
<212> TYPE: DNA
<213> ORGANISM: Artificial
<220> FEATURE:
<223> OTHER INFORMATION: Synthetic
<220> FEATURE:
<223> OTHER INFORMATION: Synthetic
<220> FEATURE:
<221> NAME/KEY: misc_feature
<222> LOCATION: (56)..(56)
<223> OTHER INFORMATION: c is linked to a propanediol spacer (C3)

<400> SEQUENCE: 111
gaattatatt cttagcgttt tataattcga aaataattct tagcgttttt attttc          56
```

THERMOSTABLE POLYMERASE INHIBITOR COMPOSITIONS AND METHODS

CROSS-REFERENCE TO RELATED APPLICATIONS

This application is a continuation of U.S. Ser. No. 16/305,858 filed on Nov. 29, 2018, which is a 371 US National Phase of International Application No. PCT/US2017/036225 filed on Jun. 6, 2017, which claims benefit of and priority to U.S. Ser. No. 62/347,004 filed on Jun. 7, 2016, each of which is incorporated herein by reference in its entirety for all purposes.

CROSS-REFERENCE TO A SEQUENCE LISTING

This application includes a sequence listing which has been submitted electronically in ASCII format and is hereby incorporated by reference in its entirety. This ASCII copy, created on Jun. 6, 2017, is named CPHDP012WO_2017-06-06_SeqList.txt and is 20795 bytes in size.

TECHNICAL FIELD

This disclosure relates generally to nucleic acid inhibitors of thermostable polymerase activity, compositions comprising the inhibitors, and methods of their use. The nucleic acid inhibitors can adapt a secondary structure to reversibly inhibit thermostable polymerases, wherein the inhibitory activity is temperature dependent. The inhibitors are useful for methods and assays which include nucleic acid synthesis by the thermostable polymerase wherein the methods and assays benefit from utilizing a hot start method.

BACKGROUND

In vitro synthesis of nucleic acid target sequences, the foundation of numerous research assays and diagnostic products, often relies in part on the use of thermostable DNA polymerases and at least one oligonucleotide primer which is designed to specifically bind to a target nucleic acid substrate in a sample suspected of containing the target. While assays using the polymerase and primer(s) are designed to generate a specific sequence, it is well known that if the assay requires a period of time at a lower or ambient temperature, the target-specific primers may hybridize to non-target sequences or may form primer dimers, resulting in mispriming and the subsequent generation of non-specific products. Such products are undesirable as they can mask the product of interest as well as prematurely deplete the reaction mixture of necessary reagents.

A primary means for reducing the effects of mispriming is to reversibly inhibit the thermostable polymerase activity at lower temperatures where such mispriming is more likely to occur. Upon increasing the temperature of the polymerase reaction mix to temperatures approximating the optimal reaction temperature of the thermostable polymerase, the inhibitory activity is removed and the thermostable polymerase extends primer(s) bound to substrate nucleic acid molecules. This method of reversibly inhibiting a thermophilic DNA polymerase to prevent primer extension at lower temperatures is referred to as "hot-start."

Hot start may be accomplished by various physical, chemical, or biochemical methods. In a physical hot start, the DNA polymerase or one or more reaction components that are essential for DNA polymerase activity is not allowed to contact the sample DNA until all the components required for the reaction are at a high temperature (Horton, R. M. et al., Biotechniques, 16; 42-43, 1994). Chemical hot start refers to a method which involves use of a DNA polymerase which is inactivated chemically but reversibly, such that the polymerase is inhibited at ambient temperatures and most active at higher temperatures (U.S. Pat. Nos. 5,773,258 and 6,183,998). Another way of implementing a hot start is to combine the DNA polymerase enzyme with an anti-DNA polymerase antibody before adding it to the reagent. The antibody inhibits the polymerase activity at ambient temperature but at the high polymerase reaction temperature, the antibody is denatured and dissociates from the polymerase, allowing activation of the polymerase (Sharkey et al., Bio/Technology, 12:506-509 (1994); Kellogg et al., Biotechniques, 16: 1134-1137 (1994)).

Another method for inhibiting thermophilic DNA polymerase at ambient temperatures involves the use of a nucleic acid aptamer which binds to and inhibits the DNA polymerase (U.S. Pat. No. 6,183,967). Aptamers are nucleic acid molecules having specific binding affinity to molecules through interactions other than classic Watson-Crick base pairing. Various aptamers have been selected and designed to exhibit specificity and affinity for thermostable polymerases and have been shown to be capable of reversibly inhibiting the polymerases. As with other reversible inhibitors of thermostable polymerases, aptamers are designed to bind and inhibit a thermostable polymerase at ambient temperatures. A subsequent increase in temperature results in the dissociation of the aptamer from the thermostable polymerase to allow primer extension and/or nucleic acid amplification at high reaction temperatures.

When designing and selecting an inhibitory aptamer for use in a reaction requiring thermostable polymerase activity, it is important to generate aptamers that bind and inhibit the polymerase in the appropriate temperature range, such as the temperature range for optimal polymerase activity, but which also dissociate from the polymerase at temperatures which allow optimal thermostable polymerase activity at temperatures when selected primers are hybridized to a target nucleic acid substrate. Described herein are aptamers which can form a secondary structure and which can reduce generation of non-specific polymerase products in various assays which rely on thermostable polymerase activity but which can dissociate from the polymerase to facilitate target product generation and detection.

BRIEF SUMMARY

In one aspect, an aptamer is provided, wherein the aptamer comprises in a 5' to 3' direction: a first nucleotide sequence comprising TATAATTGCAAAATAA (SEQ ID NO:1) or a variant thereof or TTATTTTGCAATTATA (SEQ ID NO:2) or a variant thereof; a second nucleotide sequence comprising TTCTTAGCGTTT (SEQ ID NO:3) or a variant thereof, a third nucleotide sequence comprising SEQ ID NO:1 or a variant thereof or SEQ ID NO:2 or a variant thereof; and a fourth nucleotide sequence comprising SEQ ID NO:3 or a variant thereof, wherein the first sequence is complementary to the second sequence.

In some embodiments, the aptamer has a secondary structure wherein the first and third nucleotide sequences hybridize at temperatures below about 45° C., 42° C., 40° C., 39° C., or 38° C. to form a stem and each of the second and third nucleotide sequences remain single stranded to form a loop, wherein the stem is positioned between the loops formed by the second and third nucleotide sequences.

In some embodiments, a covalent bond is present between the 5' end of the first sequence and the 3' end of the fourth sequence. In other embodiments, the covalent bond is a phosphodiester bond.

In some embodiments, the variant of SEQ ID NO:1 comprises 1, 2, 3 or 4 nucleotide substitutions and the third nucleotide sequence is complementary to the variant of SEQ ID NO:2 wherein there are no mismatches between SEQ ID NO:1 and SEQ ID NO:2.

In some embodiments, the variant of SEQ ID NO:2 comprises 1, 2, 3 or 4 nucleotide substitutions and the first nucleotide sequence is complementary to the variant of SEQ ID NO:2 wherein there are no mismatches between SEQ ID NO:1 and SEQ ID NO:2.

In some embodiments, each of the first sequence and the third sequence is 14-18, 15-16 or 16-17 nucleotides in length. In still other embodiments, each of the first sequence and the third sequence is 14, 15, 16, 17 or 18 nucleotides in length. In a particular embodiment, each of the first sequence and the third sequence is 16 nucleotides in length.

In some embodiments, the first sequence comprises SEQ ID NO:1 and the second sequence comprises SEQ ID NO:2. In still other embodiments, the first sequence consists of SEQ ID NO:1 and the second sequence consists of SEQ ID NO:2.

In some embodiments, the first sequence is selected from the group consisting of SEQ ID NO: 11-41 or a variant thereof, wherein the variant comprises 1, 2, 3 or 4 nucleotide substitutions. In other embodiments, the third sequence is the same length as the first sequence, and the third sequence is complementary to the first sequence, wherein there are no mismatches between the first sequence and the third sequence. In still other embodiments, the first sequence is selected from the group consisting of SEQ ID NO:11-41.

In some embodiments, the second sequence is identical to the fourth sequence along the entire length of the second and fourth sequences.

In some embodiments, each of the second and fourth sequences is 12 nucleotides in length.

In some embodiments, the second sequence comprises SEQ ID NO:3 and the fourth sequence comprises SEQ ID NO:3. In other embodiments, the second sequence consists of SEQ ID NO:3 and the fourth sequence consists of SEQ ID NO:3.

In some embodiments, the aptamer does not have a 5' end or a 3' end.

In some embodiments, the aptamer comprises a 5' end and a 3' end, wherein there is no covalent bond between 2 nucleotides within the first sequence or within the second sequence. In other embodiments, there is no covalent bond between nucleotides 1 and 2, 2 and 3, 3 and 4, 4 and 5, 5 and 6, 6 and 7, 7 and 8, 8 and 9, 9 and 10, 10 and 11, 11 and 12, 12 and 13, 13 and 14, 14 and 15 or 15 and 16 of SEQ ID NO:1 or of SEQ ID NO:2.

In a some embodiments, the first sequence comprises SEQ ID NO:1 and the third sequence comprises SEQ ID NO:2, and there is no phosphodiester bond between nucleotides 8 and 9 of SEQ ID NO:1. In other embodiments, the first sequence comprises SEQ ID NO:2 and the third sequence comprises SEQ ID NO:1, and there is no phosphodiester bond between nucleotides 8 and 9 of SEQ ID NO:2.

In some embodiments, the first and third sequences of the aptamer are hybridized to each other in a double stranded configuration. In other embodiments, the first and third sequences of the aptamer are hybridized to each other in a double stranded configuration when the aptamer is in a solution at 25° C. or at 37° C. In still other embodiments, the solution has a pH of about 6 to 8.

In some embodiments, both the second sequence and the fourth sequence are in a single stranded configuration. In other embodiments, both the second sequence and the fourth sequence are in a single stranded configuration when the aptamer is in a solution at 25° C. or at 37° C. In still other embodiments, the solution has a pH of about 6 to 8.

In some embodiments, the aptamer has a melting temperature ranging from about 40° C. to 50° C., 45° C. to 65° C., 45° C. to 60° C., 45° C. to 55° C., 45° C. to 50° C., 50° C. to 65° C. or 50° C. to 60° C.

In some embodiments the aptamer comprises a sequence selected from the group consisting of SEQ ID NO:42-53 or a variant thereof wherein the variant comprises 1, 2, 3 or 4 nucleotide substitutions. In other embodiments, embodiments the aptamer comprises a sequence selected from the group consisting of SEQ ID NO:42-53. In still other embodiments, the aptamer has a 5' end and a 3' end.

In some embodiments, the 5' end of the aptamer comprises a phosphate group. In other embodiments, the 3' end of the aptamer comprises a phosphate group. In still other embodiments, the 5' and the 3' end each comprise a phosphate group.

In still other embodiments, the 3' end of the aptamer is linked to a 3' capping moiety. In yet another embodiment, the 5' end of the aptamer is linked to a 5' capping moiety. In still other embodiments, the 3' end of the aptamer is linked to the 5' capping moiety and the 3' end of the aptamer is linked to the 5' capping moiety.

In some embodiments, the 5' capping moiety is selected from the group consisting of an amine group and an inverted deoxythymidine cap.

In some embodiments, the 3' capping moiety linked to the 3' end is selected from the group consisting of a phosphate, an inverted deoxythymidine cap and a propanediol spacer (C3).

In some embodiments, the aptamer comprises CAAAATAATTCTTAGCGTTTTTATTTTGCAATTATAT-TCTTAGCGTTTTATAATT G-C3 (SEQ ID NO:106); CAAAATAATTCTTAGCGTTTTTATTTTGGAATTATAT-TCTTAGCGTTTTATAATT C-C3 (SEQ ID NO:107); GAAAATAATTCTTAGCGTTTTTATTTTCGAATTATAT-TCTTAGCGTTTTATAATT C-C3 (SEQ ID NO:108); CAATTATATTCTTAGCGTTTTATAATTGGAAAATAAT-TCTTAGCGTTTTTATTTT C-C3 (SEQ ID NO:109); CAATTATATTCTTAGCGTTTTATAATTGCAAAATAAT-TCTTAGCGTTTTTATTTT G-C3 (SEQ ID NO:110); or GAATTATATTCTTAGCGTTTTATAATTCGAAAATAAT-TCTTAGCGTTTTTATTTT C-C3 (SEQ ID NO:111). In other embodiments, there is no covalent bond between the first nucleotide and the last nucleotide of the aptamer comprising the sequence of one of SEQ ID NO:106-111.

In another aspect, an aptamer is provided wherein the aptamer comprises in a 5' to 3' direction a first polynucleotide comprising SEQ ID NO:4 or a variant thereof or SEQ ID NO:5 or a variant thereof, a second polynucleotide comprising SEQ ID NO:3 or a variant thereof, a third polynucleotide comprising SEQ ID NO:5 or a variant thereof or SEQ ID NO:4 or a variant thereof, and a fourth polynucleotide comprising SEQ ID NO:3 or a variant thereof or SEQ ID NO:5 or a variant thereof, wherein each of the second and fourth sequences are 14-18 nucleotides in length, are equal in length, and are complementary to each other along their entire length; and wherein the aptamer comprises a 5' end and a 3' end.

In some embodiments, the first polynucleotide and the third polynucleotide anneal to each other to form a stem.

In some embodiments, each of the second and fourth polynucleotides do not anneal to another region of the aptamer and each of the second and fourth polynucleotides form a first and a second loop.

In some embodiments, the stem is positioned between the first and second loops.

In some embodiments, the 3' end of the fourth sequence is covalently bound to the 5' end of the first sequence and there is no phosphodiester bond between 2 nucleotides within the fourth sequence.

In some embodiments, the 3' end of the fourth sequence is covalently bound to the 5' end of the first sequence and there is no phosphodiester bond between the last nucleotide of the third sequence and the first nucleotide of the fourth sequence.

In some embodiments, there is no phosphodiester bond between nucleotides 1 and 2, 2 and 3, 3 and 4, 4 and 5, 5 and 6, 6 and 7, 7 and 8, 8 and 9, 9 and 10, 10 and 11 or 11 and 12 of SEQ ID NO:3 in the fourth sequence.

In some embodiments, the first polynucleotide comprises the sequence selected from the group consisting of SEQ ID NOs:54-77.

In some embodiments, the first polynucleotide and the third polynucleotide are the same length. In still other embodiments, there is no mismatch between the first polynucleotide and the third polynucleotide.

In some embodiments, the first sequence is identical to the third sequence along the entire length of the first and third sequences.

In some embodiments, each of the first and third sequences is 12 nucleotides in length.

In some embodiments, the first sequence comprises SEQ ID NO:3 and the third sequence comprises SEQ ID NO:3. In other embodiments, the first sequence consists of SEQ ID NO:3 and the third sequence consists of SEQ ID NO:3.

In some embodiments, the aptamer comprises a sequence selected from the group consisting of SEQ ID NOs:82-105.

In some embodiments, the 5' end of the aptamer comprises a phosphate group. In other embodiments, the 3' end of the aptamer comprises a phosphate group. In still other embodiments, the 5' and the 3' end each comprise a phosphate group.

In still other embodiments, the 3' end of the aptamer is linked to a 3' capping moiety. In yet another embodiment, the 5' end of the aptamer is linked to a 5' capping moiety. In still other embodiments, the 3' end of the aptamer is linked to the 5' capping moiety and the 3' end of the aptamer is linked to the 5' capping moiety.

In some embodiments, the 5' capping moiety is selected from the group consisting of an amine group and an inverted deoxythymidine cap.

In some embodiments, the 3' capping moiety linked to the 3' end is selected from the group consisting of a phosphate, an inverted deoxythymidine cap and a propanediol spacer (O3).

In one aspect, a composition is provided comprising a thermostable polymerase and an aptamer according to any of the foregoing aspects and embodiments, wherein the aptamer inhibits the activity of the polymerase.

In some embodiments, the molar ratio of aptamer:polymerase in the composition ranges from about 1:1 to 20:1, 2:1 to 15:1, 5:1 to 20:1, 10:1 to 20:1, 12:1 to 18:1, 14:1 to 16:1, 1:1 to 10:1, 5:1 to 10:1, or 12:1 to 18:1. In other embodiments, the molar ratio of aptamer:polymerase in the composition is about 1:1, 2:1, 4:1, 5:1, 8:1, 10:1, 11:1, 12:1, 13:1, 14:1, 15:1, 16:1, 17:1, 18:1, 19:1 or 20:1.

In some embodiments, the polymerase is selected from the group consisting of *Thermus aquaticus*, *Thermus thermophilus*, or *Thermus maritima*.

In some embodiments, the composition further comprises deoxyribonucleotide triphosphates and a divalent metal cation.

In some embodiments, the composition further comprises a forward primer. In other embodiments, the composition comprises both the forward primer and a reverse primer. In still other embodiments, the forward and/or reverse primer is specific for a target nucleic acid.

In some embodiments, the composition is a dried composition.

In some embodiments, the composition is a liquid composition.

In one aspect, a method for extending a primer is provided wherein the method comprises mixing the primer with a thermostable polymerase and an aptamer according to any of the foregoing aspects and embodiments to form a reaction mixture.

In some embodiments, the primer is specific for a target nucleic acid sequence.

In some embodiments, the method further comprises adding a reverse primer. In other embodiments, the reverse primer is specific for the target nucleic acid sequence.

In some embodiments, the method further comprises adding to the reaction mixture deoxyribonucleotide triphosphates and a divalent metal cation.

In some embodiments, the aptamer inhibits, reduces or eliminates the polymerase activity at a temperature below 45° C., 40° C., 37° C., 35° C., 32° C., or 30° C.

In one aspect, a kit is provided wherein the kit comprises a composition comprising an aptamer according to any of the foregoing aspects and embodiments and a thermostable polymerase.

In some embodiments, the kit further comprises a forward and a reverse primer, each of which is specific for a target nucleic acid sequence.

In some embodiments, the kit comprises primers and at least one probe for detecting and/or determining a sequence of the target nucleic acid sequence.

In some embodiments, the composition further comprises a forward oligonucleotide primer which is specific for the target nucleic acid sequence. In other embodiments, the composition further comprises a reverse oligonucleotide primer, which is specific for the target nucleic acid sequence.

In some embodiments, the kit further comprises a reverse transcriptase.

In some embodiments, the composition further comprises a reverse transcriptase.

In some embodiments, the composition is a dried composition.

In some embodiments, the composition is a liquid composition.

These and other objects and features of the invention will become more fully apparent when read in conjunction with the following detailed description.

BRIEF DESCRIPTION OF THE FIGURES

FIGS. 1A and 1B illustrate a closed aptamer having no 5' and 3' ends (1A) and an oligonucleotide sequence which can be synthesized to generate the closed aptamer shown in FIG. 1A (1B).

FIGS. 3A and 3B illustrate a hairpin aptamer having a 3' overhang (FIG. 3A) and an oligonucleotide sequence (FIG. 3B) which can be synthesized to generate the open predicted hairpin aptamer shown in FIG. 3A. The underline indicates the two portions of a loop sequence comprising TTCT-TAGCGTTT (SEQ ID NO:3) wherein the absence of a covalent bond (e.g., phosphodiester bond) between two nucleotides within SEQ ID NO:3 allows formation of a predicted hairpin structure at ambient temperatures.

DETAILED DESCRIPTION

Figures 2A, 2B:
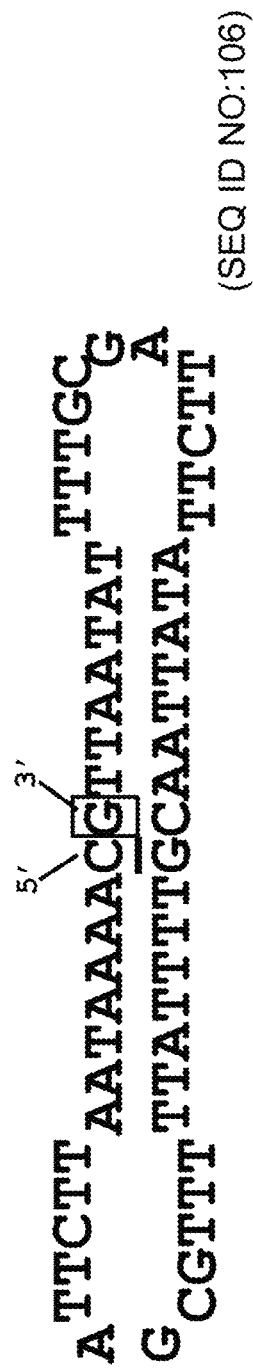
FIGS. 2A and 2B illustrate an aptamer having a 5' end (underlined C) and a 3' end (boxed G) (FIG. 2A) and an oligonucleotide sequence (FIG. 2B) which can be synthesized to generate the open aptamer shown in FIG. 2A. In this illustration of an open aptamer having the predicted structure of a stem between two loops, there is no covalent bond between the 5'C and the 3'G.

Various aspects now will be described more fully hereinafter. Such aspects may, however, be embodied in many different forms and should not be construed as limited to the embodiments set forth herein; rather, these embodiments are provided so that this disclosure will be thorough and complete, and will fully convey its scope to those skilled in the art.

The practice of the present disclosure will employ, unless otherwise indicated, conventional methods of chemistry, biochemistry, and pharmacology, within the skill of the art. Such techniques are explained fully in the literature. See, e.g.; A. L. Lehninger, *Biochemistry* (Worth Publishers, Inc., current addition); Morrison and Boyd, *Organic Chemistry* (Allyn and Bacon, Inc., current addition); J. March, *Advanced Organic Chemistry* (McGraw Hill, current addition); *Remington: The Science and Practice of Pharmacy*, A. Gennaro, Ed., 20$^{th}$ Ed.; *Goodman & Gilman The Pharmacological Basis of Therapeutics*, J. Griffith Hardman, L. L. Limbird, A. Gilman, 10$^{th}$ Ed.

Where a range of values is provided, it is intended that each intervening value between the upper and lower limit of that range and any other stated or intervening value in that stated range is encompassed within the disclosure. For example, if a range of 1% to 8% is stated, it is intended that 2%, 3%, 4%, 5%, 6%, and 7% are also explicitly disclosed, as well as the range of values greater than or equal to 1% and the range of values less than or equal to 8%.

I. Definitions

It must be noted that as used herein and in the appended claims, the singular forms "a", "an", and "the" include plural reference unless the context clearly dictates otherwise.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the methodologies which are reported in the publications which might be used in connection with the invention.

The phrase "nucleic acid" or "polynucleotide" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, or non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

As used herein, the term "thermostable polymerase" or "thermophilic polymerase" refers to an enzyme that is relatively stable to heat when compared, for example, to nucleotide polymerases from *E. coli*, and which catalyzes the template-dependent polymerization of nucleoside triphosphates. A "thermostable polymerase," will, e.g., retain enzymatic activity for polymerization and exonuclease activities when subjected to the repeated heating and cooling cycles used in PCR. Preferably, a "thermostable nucleic acid polymerase" has optimal activity at a temperature above 45° C., or at a temperature ranging from 40° C. to 80° C. and more preferably from 55° C. to 75° C. A representative thermostable polymerase enzyme isolated from *Thermus aquaticus* (Taq) is described in U.S. Pat. No. 4,889,818 and a method for using it in conventional PCR is described in Saiki et al., 1988, Science 239:487. Other thermostable DNA polymerases include, but are not limited to, DNA polymerases from thermophilic Eubacteria or Archaebacteria, for example, *T. thermophilus, T. bockianus, T. flavus, T. rubber, Thermococcus litoralis, Pyroccocus furiousus, P. wosei, Pyrococcus* spec. KGD, *Thermatoga maritime, Thermoplasma acidophilus*, and *Sulfolobus* spec. Reverse transcriptases functional between 55-60° C. include, but are not limited to, MmLV reverse transcriptase, AMV reverse transcriptase, RSV reverse transcriptase, HIV-1 reverse transcriptase, and HIV-2 reverse transcriptase.

The term "aptamer" as used herein refers to a nucleic acid that has a specific binding affinity for a target molecule, such as a protein. Like all nucleic acids, a particular nucleic acid ligand may be described by a linear sequence of nucleotides (A, U, T, C and G), typically 30-75 nucleotides long. Aptamers may also be described in terms of regions of predicted secondary structure wherein a single strand portion of the aptamer is complementary to another single strand portion of the same aptamer and thereby can hybridize (anneal) to each other to form a duplex which is referred to herein as a "stem," and portions of the aptamer which are predicted not to hybridize with other portions of the same aptamer are referred to herein as "loops." Generally, each end of a loop is linked to an end of a stem thereby providing a loop configuration.

The term "capping moiety" refers to a moiety attached to the 3' or 5' end of an aptamer or other nucleic acid that changes the stability of the nucleic acid, prevents polymerase elongation of the nucleic acid, and/or increases the efficiency of nucleic acid dimer formation. By "cap structure" is meant chemical modifications, which have been incorporated into the ends of oligonucleotide (see, for example, Matulic-Adamic et al., U.S. Pat. No. 5,998,203). In non-limiting examples: a suitable 5'-cap can be one selected from the group comprising inverted abasic residue; 4',5'-methylene nucleotide; 1-(beta-D-erythrofuranosyl) nucleotide, 4'-thio nucleotide; carbocyclic nucleotide; 1,5-anhydrohexitol nucleotide; L-nucleotides; alpha-nucleotides; modified base nucleotide; phosphorodithioate linkage; threo-pentofuranosyl nucleotide; acyclic 3',4'-seco nucleotide; acyclic 3,4-dihydroxybutyl nucleotide; acyclic 3,5-dihydroxypentyl nucleotide, 3'-3'-inverted nucleotide moiety; 3'-3'-inverted abasic moiety; 3'-2'-inverted nucleotide moiety; 3'-2'-inverted abasic moiety; 1,4-butanediol phosphate; 3'-phosphoramidate; hexylphosphate; aminohexyl phosphate; 3'-phosphate; 3'-phosphorothioate; phosphorodithioate; or bridging or non-bridging methylphosphonate moiety.

In another non-limiting example, a suitable 3'-cap can be selected from a group comprising, 4',5'-methylene nucleotide; 1-(beta-D-erythrofuranosyl) nucleotide; 4'-thio nucleotide, carbocyclic nucleotide; 5'-amino-alkyl phosphate; 1,3-diamino-2-propyl phosphate; 3-aminopropyl phosphate; 6-aminohexyl phosphate; 1,2-aminododecyl phosphate; hydroxypropyl phosphate; 1,5-anhydrohexitol nucleotide; L-nucleotide; alpha-nucleotide; modified base nucleotide; phosphorodithioate; threo-pentofuranosyl nucleotide; acyclic 3',4'-seco nucleotide; 3,4-dihydroxybutyl nucleotide; 3,5-dihydroxypentyl nucleotide, 5-5-inverted nucleotide moiety; 5-5-inverted abasic moiety; 5'-phosphoramidate; 5'-phosphorothioate; 1,4-butanediol phosphate; 5'-amino; bridging and/or non-bridging 5'-phosphoramidate, phosphorothioate and/or phosphorodithioate, bridging or non bridging methylphosphonate and 5'-mercapto moieties. For more details, see Beaucage and Iyer, 1993, Tetrahedron 49:1925, which is incorporated by reference herein.

A "variant" of a first nucleic acid sequence refers to a second nucleic acid sequence that has one or more nucleotide substitutions relative to the first nucleic acid sequence.

"Primers" refer to single-stranded oligonucleotides which are complementary to sequence portions on a template nucleic acid molecule separated by a variable number of nucleotides. Primers annealed to the template nucleic acid can be extended by covalent bonding of nucleotide monomers during amplification or polymerization of a nucleic acid molecule catalyzed by the thermostable polymerases. Typically, primers are from 12 to 35 nucleotides in length and are preferably from 15 to 20 nucleotides in length. Primers are designed from known parts of the template, one complementary to each strand of the double strand of the template nucleic acid molecule, lying on opposite sides of the region to be synthesized. Primers can be designed and synthetically prepared as is well known in the art.

The term used herein "forward primer" means a primer complementary to a strand of a nucleic acid sequence aligned in a 3' to 5' direction. The "reverse primer" has a complementary sequence to the other strand of the nucleic acid sequence.

"Template" as used herein refers to a double-stranded or single-stranded nucleic acid molecule, which serves a substrate for nucleic acid synthesis. In the case of a double-stranded DNA molecule, denaturation of its strands to form a first and a second strand is performed before these molecules may be used as substrates for nucleic acid synthesis. A primer, complementary to a portion of a single-stranded nucleic acid molecule serving as the temple template is hybridized under appropriate conditions and an appropriate polymerase may then synthesize a molecule complementary to the template or a portion thereof. The newly synthesized molecule may be equal or shorter in length than the original template.

A "target" or "target nucleic acid" refers to a single or double stranded polynucleotide sequence sought to be copied or amplified in a reaction which includes a polymerase and an oligonucleotide primer.

The term "hybridize" as used herein refers to the binding, duplexing, or hybridizing of a nucleic acid molecule preferentially to a particular nucleotide sequence. Hybridization generally involves the formation of hydrogen bonds between two single strands of a polynucleotide.

The term "complementary" as used herein refers to the capacity for precise pairing between two nucleotides; i.e., if a nucleotide at a given position of a nucleic acid is capable of hydrogen bonding (e.g., via standard Watson-Crick base pairing and Hoogsteen-type hydrogen bonding) with a nucleotide of another nucleic acid to form a canonical base pair, then the two nucleic acids are considered to be complementary to one another at that position.

Complementarity between two single-stranded nucleic acid molecules may be "partial." Complementarity is "complete," fully," or "100%" when there are no mismatches between the two single-stranded nucleotide sequences. "100% complementarity along the full length of the sequences" indicates that there are no mismatches between two nucleic acid strands which can hybridize and which are of identical length.

The term "oligonucleotide" as used herein refers to a sequence of nucleotide monomers, each bound to an adjacent nucleotide monomer by a covalent bond. An "oligonucleotide" may also include a non-nucleotide subunit or a nucleotide analog within the sequence of nucleotide monomers wherein the non-nucleotide subunit or nucleotide analog is bound to an adjacent subunit, analog or nucleotide by a covalent bond. bound by means of a covalent bond.

The covalent bond between two adjacent nucleotide monomers in an oligonucleotide is a phosphodiester bond.

The term "dried" herein refers to a composition which has a water content of less than about 10%, 8%, 5%, 4%, 3%, 2%, 1% or 0.5%.

The "polymerase chain reaction" ("PCR") is a reaction in which replicate copies are made of a target polynucleotide using one or more primers, and a catalyst of polymerization, such as a DNA polymerase, and particularly a thermally stable polymerase enzyme. Generally, PCR involves repeatedly performing a "cycle" of three steps: "melting," in which the temperature is adjusted such that the DNA dissociates to single strands, "annealing," in which the temperature is adjusted such that oligonucleotide primers are permitted to match their complementary base sequence using base pair recognition to form a duplex at one end of the span of polynucleotide to be amplified; and "extension" or "synthesis," which may occur at the same temperature as annealing, or in which the temperature is adjusted to a slightly higher and more optimum temperature, such that oligonucleotides that have formed a duplex are elongated with a DNA polymerase. This cycle is then repeated until the desired amount of amplified polynucleotide is obtained. Methods for PCR amplification are taught, for example, in U.S. Pat. Nos. 4,683,195 and 4,683,202.

"Specificity" in primer extension or PCR amplification refers to the generation of a single, "specific" PCR product with the size and sequence predicted from the sequences of the primers and the genomic or transcribed region of nucleic acid to which the primers were designed to anneal in a base-complementary manner. "Nonspecific" PCR product has a size or sequence different from such prediction.

A "target nucleic acid" is that genomic or transcribed region of nucleic acid, the ends of which are base-complementary (with proper orientation) to primers included in a complete set of PCR reagents. A primer refers to a nucleic acid sequence, which is complementary to a known portion of a target nucleic acid sequence and which is necessary to initiate synthesis by DNA polymerase. "Proper orientation" is for the two primers to anneal to opposite strands of double-stranded target nucleic acid with their 3' ends pointing toward one another. Such primers are said to target the genomic or transcribed sequence to the ends of which they are base-complementary. An "appropriate temperature", as referred to in the claims in regard to the PCR amplifications, indicates the temperature at which specific annealing between primers and a target nucleic acid sequence occurs.

"Oligonucleotide" refers to a synthetic or natural molecule comprising a covalently linked sequence of nucleotides which are joined by a phosphodiester bond between the 3' position of the pentose of one nucleotide and the 5' position of the pentose of the adjacent nucleotide.

"Primer extension assay" refers to an in vitro method wherein a primer hybridized to a complementary sequence part of a single-stranded nucleic acid template molecule is extended by sequential covalent bonding of nucleotides to the 3' end of the primer forming a new DNA molecule complementary to the DNA template molecule. The primer extension method transforms a single-stranded nucleic acid template into a partially or completely double-stranded nucleic acid molecule. The primer extension method as used herein is a single step nucleic synthesis process without amplification of the copy number of the template nucleic acid molecule.

The term "modulate" or "regulate," as used herein, refers to a change in the activity of pyruvate dehydrogenase kinase (PDK). For example, modulation or regulation may cause an increase or a decrease in protein activity, binding characteristics, or any other biological, functional or immunological properties of the PDK.

The procedures disclosed herein which involve the molecular manipulation of nucleic acids are known to those skilled in the art. See generally Fredrick M. Ausubel et al. (1995), "Short Protocols in Molecular Biology," John Wiley and Sons, and Joseph Sambrook et al. (1989), "Molecular Cloning, A Laboratory Manual," second ed., Cold Spring Harbor Laboratory Press, which are both incorporated by reference.

II. Aptamer Inhibitors of Polymerase Activity

The present disclosure provides reversible inhibitors of thermostable polymerases for use in reactions which require primer extension by the polymerase. These reversible inhibitors are aptamers, nucleic acids which are designed to adopt a secondary structure comprising a stem and a loop. The aptamers are useful in reactions and assays that benefit from incorporating hot start and can improve the sensitivity and specificity of nucleic acid synthesis.

In some embodiments, the aptamer has a "dumbbell" structure (see, e.g., FIGS. 1A and 2A). The dumbbell aptamer can exist as a "closed" structure which has no 5' or 3' terminus (illustrated in FIG. 1A) due to ligation of the 5' and 3' ends of a synthesized oligonucleotide. For example, a closed dumbbell aptamer can be generated by synthesizing a linear oligonucleotide having the sequences provided herein, allowing annealing to form the predicted dumbbell structure, then ligating the 5' and 3'. In some embodiments, the dumbbell aptamer is synthesized in a way to create 5' and 3' termini that are positioned adjacent to one another within the stem of the folded aptamer.

An example of a linear oligonucleotide which is predicted to fold into an aptamer with a stem and two loops is provided in FIGS. 1B and 2B, where 5' and 3' portions of the linear oligonucleotide hybridize to an internal complementary sequence in the same oligonucleotide to form a stem structure in which the 5' and 3' ends of the linear oligonucleotide are adjacent to one another. FIG. 1A shows an aptamer structure formed from the oligonucleotide sequence shown in FIG. 1B wherein the 5' and 3' ends of the oligonucleotide of FIG. 1B are ligated together. FIG. 2A shows an aptamer structure formed from the sequence shown in FIG. 2B wherein the 5' and 3' ends of the oligonucleotide are not ligated together, leaving the aptamer with a 5' end and a 3' end wherein the 5' and 3' ends are adjacent to one another within the predicted stem structure.

Accordingly, and with reference to FIG. 1A, an aptamer is provided in which a linear oligonucleotide can fold and anneal (hybridize) to comprise a first polynucleotide sequence comprising one strand of the stem (e.g., TTAT-TTTGCAATTATA (SEQ ID NO:2, written right to left in the illustration) in FIG. 1A), a second polynucleotide sequence which does not anneal to portions of the aptamer (e.g., TTCTTAGCGTTT (SEQ ID NO:3) to form a loop, a third polynucleotide sequence which is complementary to SEQ ID NO:1 and anneals to SEQ ID NO:1 in the appropriate conditions and temperature to form the stem (e.g., TATAAT-TGCAAAATAA (SEQ ID NO:1) and a fourth polynucleotide sequence which also does not anneal to portions of the aptamer (e.g., TTCTTAGCGTTT (SEQ ID NO:3) to form a loop.

FIGS. 2A and 2B illustrate an "open" aptamer wherein the 5' and 3' ends are not ligated, i.e., the aptamer has a 5' end and a 3' end. Notably, the nucleotides at the 5' and 3' ends are adjacent to one another within the stem of the predicted aptamer secondary structure. As shown in FIG. 2B, an oligonucleotide is synthesized and modified at its 3' end. In this particular embodiment, the 3' end is attached to a propanediol spacer (C3), preventing ligation of the 5' and 3' ends to form a closed aptamer. Upon heat denaturation and cooling, 5' and 3' portions of the oligonucleotide can hybridize to the internal complementary sequence of the oligonucleotide as illustrated in FIG. 2A.

The two loops (second and fourth polynucleotide sequences as described above and illustrated in FIGS. 1A and 2A) of the dumbbell aptamer can be identical to each other or can be minor variants of one another wherein a first loop differs from a second loop by 1 or 1 nucleotides. The loops comprise the polynucleotide sequence TTCT-TAGCGTTT (SEQ ID NO:3) or a variant thereof wherein the variant contains 1 or 2 nucleotide substitutions within SEQ ID NO:3. Acceptable substitutions in the SEQ ID NO:3 are those which do not affect the reversible inhibitory activity of the aptamer by more than about 5% or 10% relative the aptamer in which the loop sequences each have SEQ ID NO:3.

The stem which is positioned between the two loops of the aptamer is a double-stranded structure (formed by hybridization or annealing of the first and third polynucleotide sequences as described above and illustrated in FIG. 1A) which is about 12 to 18 base pairs in length, however, the length of the stem can vary with the understanding that the variation may affect the temperature at which an aptamer dissociates from and no longer inhibits the polymerase activity. It is advantageous to have aptamers which vary with respect to the temperature at which they dissociate from the polymerase. Accordingly, the aptamers of the present disclosure include those that comprise a stem which is 12 to 16, 14 to 18, 14 to 17, 14 to 16, 15 to 16, 15 to 17, or 15 to 18 base pairs in length or is about 12, 13, 14, 15, 16, 17 or 18 base pairs in length. The stem is comprised of two single-stranded oligonucleotides of equal length such that the presently described aptamers are polynucleotides which comprise two single-strand oligonucleotide sequences which are 12 to 16, 14 to 18, 14 to 17, 14 to 16, 15 to 16, 15 to 17, or 15 to 18 nucleotides in length or about 12, 13, 14, 15, 16, 17 or 18 nucleotides in length and which are complementary to one another. In some embodiments, the two oligonucleotide sequences are hybridized via hydrogen bonds and no mismatches are present in the resultant stem of the aptamer. To form the aptamer comprising 2 loops and a stem, the 3' end of one single stranded stem oligonucleotide sequence is covalently bonded to the 5' end of one of the two loops while the 3' end of the second single stranded stem oligonucleotide sequence is covalently bonded to the 5' end of the second of the two loops.

The aptamers comprising two loops as presently described can be in a closed or open form. In other words, in the closed form, there are no free ends of the aptamer polynucleotide. So, while the sequence maintains a 5' to 3' orientation as is well known in the art, the aptamer does not comprise a 5' end (e.g., 5' phosphate) or a 3' end (e.g., 3' hydroxyl). Instead, every nucleotide in the aptamer is bound to the adjacent neighbor by a covalent bond. In some embodiments, the covalent bond is a phosphodiester bond. In other embodiments, every covalent bond linking the nucleotide monomers in the aptamer is a phosphodiester bond. In an alternative embodiment, one strand of the aptamer stem comprises a non-nucleotide linking moiety such as a linker comprising DMT-ethane diol phosphoroamidite (C-2 spacer).

In some embodiments, the stem structure in the aptamer lacks a covalent bond between two of the nucleotides in only one of the strands of the stem. In these embodiments, the aptamer has a 5' end and a 3' end. As all nucleotides in the stem can remain hybridized to the opposite, fully complementary strand, the 5' and 3' ends remain adjacent to one-another when the aptamer is folded into its predicted secondary structure (see, e.g., FIG. 1A). In some embodiments, the 5' end comprises a phosphate group while the 3' end comprises a hydroxyl group. In alternative embodiments, the 5' end, the 3' end or both ends are linked to a capping moiety. The capping moiety may function to stabilize the aptamer and/or to prevent polymerization initiated at the 3' end of the aptamer. It is also possible that the lack of a covalent bond and/or the presence of a capping moiety may disrupt hydrogen bond(s) between nucleotides closest to the 5' and/or 3' end but this will not necessarily affect the inhibitory activity of the aptamer.

To synthesize a aptamer having two loops and a stem according to the present disclosure, a linear oligonucleotide is synthesized in a 3' to 5' direction using routine chemical synthesis methods. To generate a closed aptamer as described above (having no 5' or 3' free ends), the desired aptamer sequence is first synthesized then denatured by heating and slowly cooled to room temperature to allow the oligonucleotide to anneal to form an aptamer having the desired predicted dumbbell structure. For example, the synthesized oligonucleotide can be denatured in a 5 mM HEPES-KOH buffer at pH 7.5 with 50 mL of a salt such as KCl at a temperature of about 95° C. then slowly cooled (about 45 minutes to 1 hour) to room temperature.

Ligation of the 5' and 3' ends can be achieved by chemical or enzymatic means (see, e.g., Example 1) after synthesis, denaturation and annealing of the oligonucleotide as described above. Enzymatic ligation can be achieved through the use of T4 ligase wherein the 5' end of the synthesized oligonucleotide is phosphorylated and incubated with T4 ligase under appropriate conditions. Chemical ligation can be performed using, e.g. cyanogen bromide, or other methods routine in the art. In some embodiments, an oligonucleotide synthesized then first modified to place an amino group at the 5' end of the oligonucleotide. The 5'-modified oligonucleotide is then incubated with imidazole-HCl (pH 6.0) and 16.7 mg EDC (1-Ethyl-e-(3-dimethylaminopropyl)carbodiimide) to ligate the 5' and 3' ends together, forming an aptamer with the predicted structure of 2 loops and a stem wherein every nucleotide within the aptamer is covalently bonded to 2 adjacent nucleotides.

To generate an aptamer having free 5' and 3' ends, the desired aptamer sequence can be chemically synthesized above wherein the first and last nucleotides in the synthetic oligonucleotide are the nucleotides which will be adjacent to one-another within a single strand of the stem structure (as described above and shown in FIGS. 2A and 2B) but lacking a covalent bond (e.g. phosphodiester bond) between the 5' and 3' ends. In some embodiments, the 5' end lacks a phosphate group. The synthetic oligonucleotide will fold under appropriate conditions to have a predicted secondary structure with two loops separated by a stem in which there is a 5' end adjacent to a 3' end in one strand of the stem. The 5'-phosphate end can be attached to a capping moiety such as an amino group or other relevant capping moiety as described herein. The 3'-hydroxyl of the oligonucleotide can be attached to a capping moiety such as a propanediol spacer C3 or other relevant capping moiety as described herein (see Example 3). The aptamer can comprise a 5' cap, a 3' cap or both a 5' cap and a 3' cap. The presence of a 5' cap and/or 3' cap can inhibit ligation of the two ends of the oligonucleotide and can also inhibit polymerization of the oligonucleotide.

Aptamers which can bind to a polymerase and inhibit the polymerase activity as described above were designed to have 2 loops comprising the sequence TTCTTAGCGTTT (SEQ ID NO:3) as was determined by Yakimovich et al. (2003, Biochem (Moscow), 68:228-235) as being responsible for binding to the polymerase and effecting inhibition of polymerase activity when bound. In some embodiments, the loop sequence of SEQ ID NO:3 has 1 or 2 nucleotide substitutions. The two loops are separated by a stem comprising two complementary sequences of equal length. Accordingly, the aptamer structure, an example of which is shown in FIG. 1, has two loops separated by a stem. While an exemplary single strand sequence of a stem is TATAATTGCAAAATAA (SEQ ID NO:1) and its complement is TTATTTTGCAATTATA (SEQ ID NO:2), it is contemplated that there may be 1, 2 or 3 base pair substitutions within the stem. Importantly, a substitution in one strand is always coupled with a complementary substitution in the complementary strand of the stem.

The stem sequence, such as that comprised of SEQ ID NO:1 paired with SEQ ID NO:2, is AT-rich. For example, the stem sequence is 12-18 base pairs in length wherein at least 14, 15, or 16 of those base pairs are A-T base pairs. In some embodiments, the stem positioned between the two loops is 16 base pairs in length and comprises 14 A-T base pairs and two G-C base pairs. The two G-C base pairs can be adjacent to one another.

As described above, the aptamer can lack a covalent bond between two nucleotides present in one of the strands within the stem portion. For example, the stem strand comprising SEQ ID NO:1 and SEQ ID NO:2 or variants thereof can lack a covalent bond between nucleotides 1 and 2, 2 and 3, 3 and 4, 4 and 5, 5 and 6, 6 and 7, 7 and 8, 8 and 9, 9 and 10, 10 and 11, 11 and 12, 12 and 13, 13 and 14, 14 and 15 or 15 and 16 of SEQ ID NO:1 or SEQ ID NO:2. Accordingly, the aptamer which lacks a covalent bond between the 2 nucleotides comprises a single 5' terminus and a single 3' terminus. As noted above, an aptamer comprising a single 5' terminus and a single 3' terminus can be chemically synthesized as a single-stranded oligonucleotide comprising the entire sequence of the aptamer. In other words, the synthesized single strand oligonucleotide comprises a 5' portion of a first stem sequence comprising SEQ ID NO:1 or a variant thereof, a first loop sequence comprising SEQ ID NO:3 or a variant thereof, a second stem sequence comprising SEQ ID NO:2 or a variant thereof, a second loop sequence or a variant thereof and the remaining 3' portion of the first stem sequence comprising SEQ ID NO:1 or a variant thereof. Once synthesized as a single strand nucleotide it can fold under appropriate conditions to have two loops separated by a single stem, wherein one strand of the stem does not have a covalent bond between 2 adjacent nucleotides. Not to be bound by theory, the lack of a covalent bond between 2 adjacent nucleotides in one strand of a predicted stem structure may allow flexibility, such as a bend, thereby facilitating interaction of each of the two predicted loop structures with the active site of the polymerase. The presence of two loops connected via a stem in the predicted dumbbell structure may increase the local concentration of the aptamer loops, leading to more efficient binding of the aptamer to the polymerase at lower temperatures such as about 25° C. to 30° C. Accordingly, less aptamer may be needed in a reaction mixture to provide the desired hot start functionality.

It was also determined that by designing a dumbbell aptamer which comprises free 5' and 3' ends (lacks a covalent bond between two nucleotides of one strand of the stem), the aptamer is still able to inhibit polymerase activity of a thermostable polymerase at temperatures at or below about 30° C. Variations in the open dumbbell aptamer sequence can affect the temperature below which polymerase activity is inhibited. In some embodiments, an open dumbbell aptamer inhibits polymerase activity at or below about 32° C., 35° C., 38° C., or 40° C. Particularly advantageous is the complete loss of polymerase activity inhibition by these open aptamer compositions at temperatures above 40° C., 45° C., 50° C. or 55° C.

Table 1 below provides exemplary first and third sequences as described above with respect to aptamers which anneal to form a predicted dumbbell structure, wherein the first and third polynucleotide sequences of an aptamer are complementary to each other and can anneal to form the predicted stem structure. It is understood that each 5' and 3' end of the first and third sequences below is ligated to one end of a loop structure. It is also understood that in some embodiments, one of the first and third polynucleotide sequences may lack a phosphodiester bond between two of the nucleotides within the first or third sequence. Additionally, any of these sequences predicted to form on strand of the predicted stem may have a nucleotide substitution at 1, 2 3 or 4 positions in the sequence. Accordingly, the opposite strand which is predicted to anneal to this strand has a fully complementary sequence.

TABLE 1

Dumbbell Aptamer Stem Sequences

| SEQ ID NO | Sequence 5' → 3' |
|---|---|
| 11 | ATATTAAAAAATTATA |
| 12 | TATAATTTTTTAATAT |
| 13 | ATATTAAAATTATA |
| 14 | TATAATTTTAATAT |
| 15 | ATATTAAAAAATTATA |
| 16 | TATAATTTTTTAATAT |
| 17 | TTATTTTAAAATTATA |
| 18 | TATAATTTTAAAATAA |
| 19 | TTATTTTAAAATTATA |
| 20 | TATAATTCCAAAATAA |
| 21 | TTATTTTGGAATTATA |
| 22 | TATAATTGCAAAATAA |
| 23 | TTATTTTGCAATTATA |
| 24 | TATAATTCGAAAATAA |
| 25 | TTATTTTCGAATTATA |
| 26 | TTATTTTAAAATTATA |
| 27 | TATAATTTTAAAATAA |
| 28 | TTATTTTCCAATTATA |
| 29 | TATAATTGGAAAATAA |
| 30 | TTATTTTGCAATTATA |
| 31 | TATAATTGCAAAATAA |
| 32 | TTATTTTCGAATTATA |
| 33 | TATAATTCGAAAATAA |
| 34 | TATTTTAAAAATAT |
| 35 | ATATTTTTAAAATA |
| 36 | TATTTTTAAAATAT |
| 37 | ATATTTTAAAAATA |
| 38 | TATTTTAAAAATAT |
| 39 | ATATTTT-C2-spacer-TAAAATA |
| 40 | TATTTTTAAAATAT |
| 41 | ATATTTT-C2-spacer-AAAAATA |

Table 2 below provides exemplary oligonucleotide sequences which can be synthesized and which are predicted to fold into an aptamer having two loops and a stem. The bolded nucleotides represent portions of a stem sequence which, when the oligonucleotide is folded as predicted, hybridizes to a second stem sequence indicated by the underlined portion.

TABLE 2

Dumbbell Aptamers Synthesized as Linear Oligonucleotides

| SEQ ID NO | Sequence 5' → 3' |
|---|---|
| 42 | CAAAATAATTCTTAGCGTTTTTATTTTGCAATTATATTCTTAGCGTTTTATAATTG |
| 43 | CAATTATATTCTTAGCGTTTTATAATTGCAAAATAATTCTTAGCGTTTTTATTTTG |
| 44 | TAAAATAATTCTTAGCGTTTTTATTTTAAAATTATATTCTTAGCGTTTTATAATTT |
| 45 | CAAAATAATTCTTAGCGTTTTTATTTTGGAATTATATTCTTAGCGTTTTATAATTC |
| 46 | GAAAATAATTCTTAGCGTTTTTATTTTCGAATTATATTCTTAGCGTTTTATAATTC |
| 47 | AAATTATATTCTTAGCGTTTTATAATTTTAAAATAATTCTTAGCGTTTTTATTTTA |
| 48 | CAATTATATTCTTAGCGTTTTATAATTGGAAAATAATTCTTAGCGTTTTTATTTTC |
| 49 | GAATTATATTCTTAGCGTTTTATAATTCGAAAATAATTCTTAGCGTTTTTATTTTC |
| 50 | AAAATATTCTTAGCGTTTATATTTTAAAATATTCTTAGCGTTTTATTTTA |
| 51 | AAAATATTCTTAGCGTTTATATTTTAAAAATATTCTTAGCGTTTTATTTTT |
| 52 | AAAATATTTCTTAGCGTTTATATTTT-C2-spacer-TAAAATATTCTTAGCGTTTTATTTTA |
| 53 | AAAATATTTCTTAGCGTTTATATTTT-C2-spacer-AAAAATATTCTTAGCGTTTTATTTTT |
| 54 | AAATTATATCTTAGCGTTTTATAATTTTTAATATTCTTAGCGTTTATATTAAA |
| 55 | AATTATATCTTAGCGTTTTATAATTTTAATATTCTTAGCGTTTATATTAA |
| 56 | AAATTATATTCTTAGCGTTTTATAATTTTTAATATTCTTAGCGTTTATATTAAA |
| 57 | AAATTATATTCTTAGCGTTTTATAATTTAAAATAATTCTTAGCGTTTTATTTTA | which is predicted to form a loop comprises TTCT-TAGCGTTT (SEQ ID NO:3).

TABLE 3

Hairpin Aptamer Stem Sequences

| SEQ ID NO | Sequence 5' → 3' |
|---|---|
| 58 | TTATTTTAAAATTATA |
| 59 | TATAATTTTAAAATAA |
| 60 | TATTTTAAAAATATA |
| 61 | TATATTTTAAAAATA |
| 62 | TTAATTTAAATTTATA |
| 63 | TATAAATTTAAATTAA |
| 64 | TTAATTTTAAAATATA |
| 65 | TATATTTTAAAATTAA |
| 66 | TTATTTTAAAAAATA |
| 67 | TATTTTTAAAAATAA |
| 68 | TTATATTAAATTATA |
| 69 | TATAATTTAAATATAA |
| 70 | TATATTTTAAAAA |
| 71 | TAATTTTAAAAATAT |
| 72 | TAATTTTAAAAAATA |
| 73 | TATTTTTAAAATTA |
| 74 | TTATTTTAAAAAAT |
| 75 | ATTTTTAAAAATAA |
| 76 | TAATTTTAAAAAT |
| 77 | ATTTTTAAAATTA |
| 78 | TAATTTTAAAAAT |
| 79 | ATTTTTAAAATTA |
| 80 | CAATTTTAAAAAT |
| 81 | ATTTTTAAAATTG |

In other embodiments described herein, the aptamer is designed to form a hairpin structure wherein the aptamer is predicted to comprise a single stem having two single strands which are complementary and terminating in a single loop. The single stem in the predicted hairpin structure as described herein comprises a first polynucleotide sequence which is annealed to a third polynucleotide sequence wherein the first and third polynucleotide sequences are complementary and are equal in length. The 3' end of the first polynucleotide sequence is covalently bound to the 5' end of a second polynucleotide sequence which is predicted to form a single stranded loop in the predicted hairpin aptamer, and the 3' end of the second polynucleotide sequence is covalently bound to the 5' end of the third polynucleotide sequence. Table 3 below provides some exemplary oligonucleotide sequences for the first and/or third polynucleotide sequences in the hairpin aptamer. It is understood that any of these sequences may have a nucleotide substitution at 1, 2 3 or 4 positions in the sequence. In preferred embodiments, the second polynucleotide sequence In some embodiments, the hairpin aptamers have 5' and/or 3' overhangs which represent a full or partial sequence of SEQ ID NO:3 or a variant thereof. An example of a hairpin aptamer according to the present disclosure is provided in FIGS. 3A and 3B. The underlined portion of FIG. 3A indicates the sequence of SEQ ID NO:3. Accordingly, the hairpin aptamer of FIG. 3A has an overhang comprising a 3' portion of SEQ ID NO:3. Specifically, FIG. 3A illustrates a hairpin aptamer in which a 3' portion of SEQ ID NO:3 (GTTT) is ligated to the 5' nucleotide of a stem strand comprising the sequence TTATTTTAAAATTATA (SEQ ID NO:58) and the remaining 5' portion of SEQ ID NO:3 is ligated to the 3' nucleotide of a second stem strand comprising the sequence TATAATTTTAAAATAA (SEQ ID NO:59). Because there is no covalent (phosphodiester) bond between nucleotides 4 and 5 of SEQ ID NO:3, the oligonucleotide of SEQ ID NO:90 (FIG. 3B) is predicted to fold into a hairpin structure as described in FIG. 3A.

To synthesize the hairpin aptamer, oligonucleotides can be chemically synthesized based on the sequences shown in Table 4 below. The underlined bases indicate the 3' and 5' portions of SEQ ID NO:3 (cut loop). The bolded bases indicate stem sequences which are fully complementary to one another and which are predicted to hybridize when the aptamer is folded into a hairpin structure. SEQ ID NO:79 illustrates a hairpin structure in which the 3' overhang represents the full loop sequence of SEQ ID NO:3 while SEQ ID NO:80 illustrates a hairpin structure in which the 5' overhang represents the full loop sequence of SEQ ID NO:3.

SEQ ID NO:84 is an example of a hairpin aptamer with a 3' overhang in which a 5' portion of a sequence consisting of SEQ ID NO:3 is covalently linked to the 3' end of one stem sequence, the remaining 3' portion of the sequence consisting of SEQ ID NO:3 is covalently linked to the 5' end of the complementary stem sequence, and there is no covalent (e.g., phosphodiester) bond between nucleotides 7 and 8 of the sequence consisting of SEQ ID NO:3.

TABLE 4

Hairpin Aptamer Synthesized as Linear Oligonucleotides

| SEQ ID NO | Sequence 5' → 3' |
|---|---|
| 82 | GCGTTTTATTTTAAAATTATATTCTTAGCGTTTTATAATTTTAAAATAATTCTTA |
| 83 | TTATTTTAAAATTATATTCTTAGCGTTTTATAATTTTAAAATAATTCTTAGCGTTT |
| 84 | TTCTTAGCGTTTTATTTTAAAATTATATTCTTAGCGTTTTATAATTTTAAAATAA |
| 85 | GCGTTTTATAATTTTAAAATAATTCTTAGCGTTTTATTTTAAAATTATATTCTTA |
| 86 | TTCTTAGCGTTTTATAATTTTAAAATAATTCTTAGCGTTTTATTTTAAAATTATA |
| 87 | TATAATTTTAAAATAATTCTTAGCGTTTTATTTTAAAATTATATTCTTAGCGTTT |
| 88 | CGTTTTATTTTAAAATTATATTCTTAGCGTTTTATAATTTTAAAATAATTCTTAG |
| 89 | AGCGTTTTATTTTAAAATTATATTCTTAGCGTTTTATAATTTTAAAATAATTCTT |
| 90 | GTTTTTATTTTAAAATTATATTCTTAGCGTTTTATAATTTTAAAATAATTCTTAGC |
| 91 | TAGCGTTTTATTTTAAAATTATATTCTTAGCGTTTTATAATTTTAAAATAATTCT |
| 92 | GCGTTTTATTTTTAAAAATATATTCTTAGCGTTTTATATTTTAAAAATATTCTTA |
| 93 | GCGTTTTAATTTAAATTTATATTCTTAGCGTTTTATAAATTTAAATTAATTCTTA |
| 94 | GCGTTTTAATTTTAAAATATATTCTTAGCGTTTTATATTTTAAAATTAATTCTTA |
| 95 | GCGTTTTATTTTTAAAAAATATTCTTAGCGTTTTATTTTTTAAAAATAATTCTTA |
| 96 | GCGTTTTATATTTAAATTATATTCTTAGCGTTTTATAATTTAAATATAATTCTTA |
| 97 | CGTTTTATTTTTAAAAAATATTCTTAGCGTTTTATTTTTTAAAAATAATTCTTAG |
| 98 | GTTTTTATTTTTAAAAAATATTCTTAGCGTTTTATTTTTTAAAAATAATTCTTAGC |
| 99 | CGTTTATATTTTTAAAAATTATTCTTAGCGTTTTAATTTTTAAAAATATTTCTTAG |
| 100 | GTTTATATTTTTAAAAATTATTCTTAGCGTTTTAATTTTTAAAAATATTTCTTAGC |
| 101 | GTTTTAATTTTAAAAAATATTCTTAGCGTTTTATTTTTTAAAATTATTCTTAGC |
| 102 | GTTTTTATTTTTAAAAAATTTCTTAGCGTTTATTTTTTAAAAATAATTCTTAGC |
| 103 | GTTTTAATTTTAAAAAATTTCTTAGCGTTTATTTTTTAAAATTATTCTTAGC |
| 104 | GTTTTAATTTTAAAAATTTCTTAGCGTTTATTTTTAAAATTATTCTTAGC |
| 105 | GTTTCAATTTTAAAAATTTCTTAGCGTTTATTTTTAAAATTGTTCTTAGC |

Aptamer Inhibition Activity

Also contemplated is a method for reversibly inhibiting polymerase activity comprising incubating an aptamer as described herein with a thermostable polymerase. The aptamers of the present disclosure were designed to bind to a thermostable polymerase and inhibit the polymerase activity of that polymerase at lower temperatures, then dissociate from the polymerase as the reaction temperature is raised. In some embodiments, the thermostable polymerase is selected from but not limited to DNA polymerases from thermophilic Eubacteria or Archaebacteria, including but not limited to, *Thermus aquaticus*, *T. thermophilus*, *T. bockianus*, *T. flavus*, *T. rubber*, *Thermococcus litoralis*, *Pyroccocus furiousus*, *P. wosei*, *Pyrococcus* spec. KGD, *Thermatoga maritime*, *Thermoplasma acidophilus*, and *Sulfolobus* spec. In some embodiments the polymerase may be a reverse transcriptase functional between 55-60° C., including but not limited to, MmLV reverse transcriptase, AMV reverse transcriptase, RSV reverse transcriptase, HIV-1 reverse transcriptase, and HIV-2 reverse transcriptase.

The ability of the aptamer to bind to and inhibit, then dissociate from the polymerase depends in part upon its secondary structure in the reaction mixture. Aptamers of the present disclosure have melting temperatures ranging from about 45° C. to 70° C. In some embodiments, the closed (ligated) dumbbell aptamers have higher melting temperatures, ranging from about 60° C. to 70° C., 60° C. to 65° C. or 65° C. to 70° C., while the open dumbbell aptamers lacking a phosphodiester bond in one strand of the stem have a melting temperature ranging from about 45° C. to 55° C., 45° C. to 50° C., 50° C. to 55° C., or 48° C. to 53° C.

Melting temperatures are determined in some embodiments at an aptamer concentration of about 8 µM in a buffered solution having a pH of about 8. The buffered solution in some embodiments comprises 3 mM $MgCl_2$, 15 KCl, 25 mM HEPES, pH 8.0. Melting temperatures for each aptamer can be measured using a UV-Vis-NIR spectrophotometer (see, e.g., Example 2).

While the loss of secondary structure of an inhibitory aptamer can result in a decrease in the aptamer's ability to remain bound to and inhibit a polymerase, dissociation from the polymerase with increasing temperatures can depend on other factors such as the primary sequence of the aptamer and the interface between the aptamer and the polymerase. Accordingly, contemplated and described are aptamers that inhibit, reduce or eliminate thermostable polymerase activity at temperatures below about 50° C., 45° C., 44° C., 43° C., 42° C., 41° C., 40° C., 39° C. or 38° C. In some embodiments, the aptamer and polymerase are in a solution having a pH of about 6-8, 6-9, 7-8, 7-9, or 8-9.

The ability of an aptamer to inhibit, reduce or eliminate the polymerase activity of a thermostable polymerase can be measured and quantified using an assay which measures the polymerase activity in the presence or absence of the aptamer at varying temperatures. It is understood that several alternative methods may be used to measure the ability of an aptamer to inhibit polymerase activity in a temperature-dependent way, only some of which are briefly described here.

One method for measuring the inhibitory effects of an aptamer on the activity of a thermostable polymerase is exemplified in Example 3 below and further described in Nikiforov et al., 2011, Analytical Biochemistry, 412: 229-236. Specifically, a hairpin template is provided in which a fluorescent label (e.g., fluorescein (FAM; 5'-Dimethoxytritylloxy-5-[N-((3',6'-dipivaloylfluoresceinyl)-aminohexyl)-3-acrylimido]-2'-deoxyUridine-3'-[(2-cyanoethyl)-(N,N-diisopropyl)]-phosphoramidite) dT residue) is incorporated near the 3' end (e.g., 2, 3, 4 or 5 bases away from the 3' end of the oligonucleotide substrate). To a PCR reaction mixture (e.g., 50 mM Tris-HCl, pH 8.3, 50 mM NaCl, 5 mM $MgCl_2$, and 2 µL of 2 mM dATP), a polymerase preparation is added wherein the polymerase is in the presence or absence of the inhibitor aptamer. In some embodiments comprising both polymerase and inhibitor aptamer, about 0.8 µM polymerase is mixed with 8 µM aptamer (1:10 ratio). In other embodiments, the polymerase/aptamer ratio is about 1:5 to 1:15 or about 1:5 or 1:15. After addition of polymerase to the PCR reaction mix containing the labeled hairpin substrate, the reaction is heated from about 25° C. to 75° C. and the FAM signal is measure using a standard dissociation curve program (e.g., Mx3005P, Agilent Technologies) to determine the temperature at which the polymerase is active, and the temperature below which the polymerase is inhibited by the aptamer.

Another method for measuring thermostable polymerase activity in the presence and absence of an aptamer involves use of an oligonucleotide substrate for the polymerase which forms a hairpin structure having a stem and a loop, wherein the stem has a long single-stranded portion which terminates at the 3' end. A quencher (e.g., N,N'-tetramethyl-rhodamine, TAMRA) is attached to the stem near the 5' end of the loop and a fluorescent dye (e.g., carboxyfluorescein, FAM) is attached to the stem near the 3' end of the loop. The fluorescence of the dye is quenched through resonance energy transfer by the quencher when the aptamer substrate is in its predicted folded structure until a oligonucleotide primer is added and allowed to anneal to the 3' end of the stem single-stranded portion and is extended to synthesize the complementary strand by the polymerase, resulting in opening of the loop and spatial separation of the quencher and dye. The polymerase and aptamer are mixed in an appropriate solution of reagents at least including nucleotide triphosphates, a divalent metal cation, an appropriate buffer and primer and fluorescence is measured over time, with fluorescence increasing at a rate proportional to the polymerase activity. The kinetics of enzymatic DNA synthesis exhibit Michaelis-Menten dependence on substrate concentration. Accordingly, inhibition profiles for various aptamers can be generated by running a series of polymerase reactions in the presence of increasing amounts of aptamer. The resulting data can be used to determine an $IC_{50}$ value for each aptamer (Summerer and Marx, Angew Chem Int, 2002, 41:3620-3622). Moreover, $IC_{50}$ values for each aptamer can be determined over a range of temperatures.

A third alternative method for measuring the ability of an aptamer as described herein to inhibit a thermostable polymerase in a temperature-dependent manner is by using a template oligonucleotide DNA molecule which is labeled at its 5' end with $^{32}P$-γ-ATP and which forms a hairpin wherein a 5' portion (e.g., 12-24 nucleotides) of the oligonucleotide is single-stranded followed by a double-stranded stem and small loop. As above, the thermostable polymerase is incubated with varying concentrations of an aptamer as described herein, then added to the substrate and standard PCR reaction mixture and the PCR reaction is allowed to proceed for a set period of time (e.g., 45 min. to 1 hour) at different temperatures (e.g., 25° C. to 75° C.), stopped by the addition of EDTA, and then resolved using polyacrylamide gel electrophoresis. Standard phosphorimager detection and quantitation methods can be used to determine polymerase activity level as only when the polymerase is active (not inhibited by the aptamer at a given temperature) will the 3' end of the hairpin substrate be extended to form a longer product which is radio-labeled and detected. As with the assays above, an $IC_{50}$ for each aptamer at a given temperature can be determined by quantitation and analysis.

The use of the aptamers described herein for hot start polymerase applications which can decrease nonspecific product generation relies on the ability of the aptamer to dissociate from the polymerase as the temperature. Accordingly, an aptamer according to the present disclosure dissociates from a thermostable polymerase when a reaction mixture containing the aptamer and the polymerase is raised to a temperature of at least about 45° C., 50° C., 55° C., 60° C., 65° C., 70° C., 75° C., or 80° C. As a loss of inhibition of the polymerase is a likely indication of aptamer dissociation from the polymerase, in other embodiments, a reversibly inhibitory aptamer of the present disclosure does not inhibit thermostable polymerase activity when the reaction mixture containing the aptamer and the polymerase is raised to a temperature of at least about 45° C., 50° C., 55° C., 60° C., 65° C., 70° C., 75° C., or 80° C. It is understood that the temperature above which an aptamer no long inhibits polymerase activity depends on the sequence, composition and inherent structure of the aptamer in solution with the polymerase. Accordingly, any aptamer sequence as described herein may be further characterized or defined by its lack of polymerase activity inhibition at or above a specified temperature.

Moreover, any aptamer sequence and predicted structure as described herein may be further characterized or defined by its ability to inhibit polymerase activity at or below a specified temperature. In some embodiments, the aptamer inhibits the polymerase by 95%-100%, 98% to 100% or by about 100% relative to polymerase activity in the absence of the aptamer at or below a temperature of about 25° C., 30° C., or 35° C. As the temperature of the mixture containing the aptamer and the polymerase is raised, there will be a corresponding loss of inhibition. Experimental studies suggest that a transition from about 95% to 100% of polymerase activity to loss of substantially all inhibition can occur over a temperature range of about 4° C. to 10° C., or 5° C. to 7° C.

Inhibition of polymerase activity by an aptamer as described herein can also be affected by the concentration of the aptamer and polymerase in a mixture or by the ratio of aptamer:polymerase. For example, the aptamer is effective in inhibiting polymerase activity when the aptamer is present in the mixture at a concentration of about 100 nM to 1000 nM, 100 nM to 500 nM, 25 nM to 750 nM, for 500 nM to 1000 nM. The aptamers described are useful for reversibly inhibiting thermostable polymerases including DNA polymerases, RNA polymerases and reverse transcriptases.

The ability of the aptamers provided herein to inhibit polymerase activity at ambient temperatures or at temperatures lower than temperatures which are optimal for polymerase activity is advantageous for at least the reason that there will be a decrease in or elimination of non-specific products generated at these lower temperatures. As shown at least in Examples 4 and 5 and FIGS. 4-5, use of the aptamers can reduce generation of non-specific products and increase production of the target amplicon(s).

Applications

As described above, aptamers of the present disclosure have the ability to reversibly inhibit thermostable polymerases at ambient temperatures or temperatures below the optimal temperatures for various thermostable polymerases. These aptamers thus can readily be applied to any applications wherein a thermostable nucleotide polymerase is used and wherein it is desirable to have the polymerase activity turned off at a lower temperature but then be able to regain its activity at a higher temperature (hot start). Such applications include but are not limited to standard PCR, reverse transcriptase PCR, in-situ PCR, quantitative PCR, and minisequencing or other reactions involving primer extension in which a thermostable polymerase present and a hot-start method is advantageous. Such methods are well known in the art. In some embodiments, the increased sensitivity and specificity provided by the disclosed compositions is useful during the amplification and analysis of DNA and RNA in medical genetics research and diagnosis, pathogen detection, forensic analysis, and animal and plant genetics applications. The methods and compositions of the present disclosure are useful in any polynucleotide synthesis reaction that requires thermostable polymerase to cycle anywhere between 40° C. and 80° C.

Examples 4 and 5 below describe PCR experiments performed using Taq polymerase in the presence or absence of an aptamer according to the present disclosure. These studies demonstrate the ability of the aptamers described herein to both decrease generation of non-specific amplification products as well as increase quantities of target amplicons in the reaction mix. Example 4 describes a biplex PCR reaction containing genomic DNA and 2 primer pairs for amplification of two target sequences. Prior to initiating a PCR reaction by addition of the thermostable polymerase, 4 units of Taq polymerase was incubated with 200 nM prior to adding the Taq to the PCR master mix. In this particular experiment, an unligated (open) dumbbell aptamer was used which was shown (Example 2) to have a melting temperature of about 42° C. Detection and analysis of fluorescence signals as well as gel analysis of the PCR products show effects on both non-specific product generation and on the quantity of target amplicon production. It is contemplated that any of the aptamers described herein which have melting temperatures below the optimal temperature of the thermostable polymerase in the reaction mix can enhance target amplicon generation and detection.

Example 5 explores varying ratios of aptamer:thermostable polymerase on non-specific product and target amplicon generation. Ratios ranging from about 2.5:1 to 15:1 were tested. While all ratios resulting in generation of the desired product, the 15:1 ratio was most effective in reducing non-specific product generation while maintaining levels of target amplicon generation.

Accordingly, contemplated herein are methods which involve using a thermostable polymerase to extend a primer which is annealed to a nucleotide template or substrate molecule. As well understood in the art, wherein the primer is extended by the polymerase in the presence of nucleotides (e.g., the deoxyribonucleotides, dATP, dGTP, dCTP, dTTP), a divalent metal cation such as $Mg^{2+}$ or $Mn^{2+}$, a buffer, and at least one primer.

In some embodiments, the inhibitors described herein may be used in combination with other hot-start technologies such as antibody-based hot start. In other embodiments, for example, two or more aptamers which dissociate from a polymerase at different temperatures may be combined in a single reaction.

Exemplary Automation and Systems

In some embodiments, a target nucleic acid sequence is copied or amplified, then detected using an automated sample handling and/or analysis platform. In some embodiments, commercially available automated analysis platforms are utilized. For example, in some embodiments, the GeneXpert® system (Cepheid, Sunnyvale, Calif.) is utilized.

The present disclosure is illustrated for use with the GeneXpert system. Exemplary sample preparation and analysis methods are described below. However, the present disclosure is not limited to a particular detection method or analysis platform. One of skill in the art recognizes that any number of platforms and methods may be utilized.

The GeneXpert® utilizes a self-contained, single use cartridge. Sample extraction, amplification, and detection may all be carried out within this self-contained "laboratory in a cartridge." (See e.g., U.S. Pat. Nos. 5,958,349, 6,403,037, 6,440,725, 6,783,736, 6,818,185; each of which is herein incorporated by reference in its entirety.)

Components of the cartridge include, but are not limited to, processing chambers containing reagents, filters, and capture technologies useful to extract, purify, and amplify target nucleic acids. A valve enables fluid transfer from chamber to chamber and contains nucleic acids lysis and filtration components. An optical window enables real-time optical detection. A reaction tube enables very rapid thermal cycling.

In some embodiments, the GenXpert® system includes a plurality of modules for scalability. Each module includes a plurality of cartridges, along with sample handling and analysis components.

After the sample is added to the cartridge, the sample is contacted with lysis buffer and released DNA is bound to a DNA-binding substrate such as a silica or glass substrate. The sample supernatant is then removed and the DNA eluted in an elution buffer such as a Tris/EDTA buffer. The eluate may then be processed in the cartridge to detect target genes as described herein. In some embodiments, the eluate is used to reconstitute at least some of the PCR reagents, which are present in the cartridge as lyophilized particles.

In some embodiments, PCR is used to amplify and detect the presence of the target nucleic acid sequence and/or a nucleic acid sequence that indicates genomic copy number. In some embodiments, the PCR uses Taq polymerase with hot start function imparted by use of an aptamer as provided herein.

Kits

Kits for detecting a nucleic acid target sequence present in solid, semi-solid, or liquid biological samples are also provided. The kit includes a reagent mix comprising a thermostable polymerase and an aptamer as described herein that can reversibly inhibit activity of the polymerase. In some embodiments, the kit can be used for detection, quantifying or sequencing any target nucleic acid. Alternatively, the kit includes one or more oligonucleotide primers (e.g., a forward and/or reverse primer) that specifically hybridize to a specified target nucleic acid and may also include labeled primers and/or probes as is routine in the art.

The kits may include instructions for obtaining biological samples and contacting them with sample buffer, for mixing the samples with sample buffer, placing labels on the apparatus and recording relevant test data; for shipping the apparatus, and the like. The kits may include instructions for reading and interpreting the results of an assay. The kits may further comprise reference samples that may be used to compare test results with the specimen samples.

EXAMPLES

Example 1

Oligonucleotide Synthesis and Ligation

Aptamers as described herein were synthesized using standard oligonucleotide synthesis methods. Oligonucleotide synthesis was performed on a MerMade 12 DNA Synthesizer (BioAutomation). Standard phosphoramidite synthesis cycles were used, and coupling time was increased to 360 seconds for modified phosphoramidites. Cleavage from the solid support and deprotection was carried in concentrated aqueous ammonia at RT for 24 hrs. HPLC analyses were done on an Agilent 1100 instrument equipped with a quaternary pump, autosampler, and diode array detector. Oligonucleotides were analyzed using reversed-phase HPLC (RP HPLC) on a C18 Gemini column (4.6 mm×250 mm, 5 um, Phenomenex) eluting with a linear gradient of acetonitrile/0.1 M triethylammonium bicarbonate, pH 7: 16-23% acetonitrile over 20 min for DMT-on oligonucleotides and 7-14% acetonitrile for oligonucleotides with DMT groups removed (DMT-off). DMT-on oligonucleotides were purified using reverse phase HPLC, DMT groups were cleaved, and the final oligonucleotide products were isolated by ethanol precipitation and quantified by UV.

Where indicated, some aptamers were modified at the 5' and/or 3' end after synthesis. 5' and 3' phosphorylation was achieved using (3-(4,4'-Dimethoxytrityloxy)-2,2-(dicarboxymethylamido)propyl-1-O-succinoyl-long chain alkylamino-CPG) (Glen Research Cat. No. 10-1901; U.S. Pat. No. 5,959,090 and EP Pat. No. EP0816368) and (3-(4,4'-Dimethoxytrityloxy)-2,2-dicarboxyethyl]propyl-(2-cyanoethyl)-(N,N-diisopropyl)-phosphoramidite) (Glen Research Cat. No. 20-2903; U.S. Pat. No. 5,959,090). Modification of the 5' end with an amino group was achieved using 5'-Amino-dT-CE Phosphoramidite (Glen Research Cat. No. 10-1932), (5'-monomethoxytritylamino-2'-deoxyThymidine, 3'-[(2-cyanoethyl)-(N,N-diisopropyl)]-phosphoramidite). Modification of the 3' end with a propanediol spacer CPG (-C3) was achieved using ((1-Dimethoxytrityloxypropanediol-3-succinoyl)-long chain alkylamino-CPG) (Cat. No. 20-2913).

To produce ligated dumbbell aptamers, oligonucleotides synthesized as above were ligated either enzymatically or chemically. For enzymatic ligation, 1 mL of 16 μM 5'-phosphate-modified oligonucleotide in a 50 mM KCl solution was heated to 95° C. for 5 min in a heating block and slowly cooled to room temperature in the same heating block by switching the power off to allow annealing (intramolecular hybridization) of the oligonucleotide. 900 μL of the annealed oligonucleotide was mixed with 100 μL T4 ligation buffer, then with 10 μL T4 ligase (New England BioLabs) and left overnight at 16° C. Ligated aptamer was purified by RP-HPLC method.

To produce chemically ligated aptamers, 5' ((amino)-T))-modified oligonucleotide (220 μM) in 5 mM HEPES-KOH buffer pH 7.5 and 50 mM KCl was denatured at 95° C. for 5 min. followed by slow (approximately 1 hr) cooling-annealing to room temperature. Then 100 μL of annealed oligonucleotide was mixed with 66.7 μL 0.1 M imidazole-HCl (pH 6.0) and 16.7 mg EDC (1-Ethyl-e-(3-dimethylaminopropyl)carbodiimide). After a brief vortexing and centrifugation, an additional 266 μL of 0.1 M imidazole-HCl (pH 6.0) was supplied to the reaction and mix was left overnight at room temperature. Ligated oligonucleotide was purified by RP-HPLC.

Example 2

Melting Temperature (Tm) Determination

UV-melt curve analysis was performed for various aptamers generated according to Example 1 above. Oligonucleotides were prepared at a concentration of 1 μM in buffer (3 mM $MgCl_2$, 15 KCl, 25 mM HEPES, pH 8.0) and analyzed using an Agilent Technologies Cary 4000 Series UV-Vis-NIR spectrophotometer and associated software according to the manufacturer's instructions. Results are presented below in Table 5. As expected, the Tm's of unligated dumbbell aptamers are lower than Tm's of the ligated dumbbell aptamers.

TABLE 5

| SEQ ID NO | Tm (° C.) | Description | Linear Oligonucleotide Sequence (5' → 3') (including terminal modifications if present) |
|---|---|---|---|
| 54 | 63.1 | Ligated (closed) dumbbell | AAATTATATCTTAGCGTTT TATAATTTTTAATATTCT TAGCGTTTATATTAAA |

TABLE 5-continued

| SEQ ID NO | Tm (° C.) | Description | Linear Oligonucleotide Sequence (5' → 3') (including terminal modifications if present) |
|---|---|---|---|
| 55 | 60.2 | Ligated (closed) dumbbell | AATTATATCTTAGCGTTTT ATAATTTTAATATTCTTAG CGTTTATATTAA |
| 56 | 62.7 | Ligated (closed) dumbbell | AAATTATATTCTTAGCGTT TTATAATTTTTTAATATTT CTTAGCGTTTATATTAAA |
| 95 | 55.3 | hairpin | GCGTTTTTATTTTAAAAA ATATTCTTAGCGTTTTATT TTTTAAAAATAATTCTTA-C3 |
| 96 | 52.9 | hairpin | GCGTTTTTATATTTAAAT TATATTCTTAGCGTTTTATA ATTTAAATATAATTCTTA-C3 |
| 97 | 55.5 | hairpin | CGTTTTTATTTTAAAAAAT ATTCTTAGCGTTTTTATTT TTTAAAAATAATTCTTAG-C3 |
| 98 | 55.5 | hairpin | GTTTTTATTTTAAAAAAT ATTCTTAGCGTTTTTATTTT TTAAAAATAATTCTTAGC-C3 |
| 99 | 56.6 | hairpin | CGTTTATATTTTAAAAATT ATTCTTAGCGTTTTAATT TTTAAAAATATTTCTTAG-C3 |
| 57 | 63 | Ligated (closed) dumbbell | AAATTATATTCTTAGCGTT TTATAATTTTAAAATAATT CTTAGCGTTTTTATTTTA |
| 88 | 55.0 | hairpin | CGTTTTTATTTTAAAATTAT ATTCTTAGCGTTTTTATAA TTTTAAAAATAATTCTTAG-C3 |
| 89 | 54.4 | hairpin | TAGCGTTTTTATTTTAAAA TTATATTCTTAGCGTTTTA TAATTTTAAAATAATTCT-C3 |
| 90 | 54.6 | hairpin | GTTTTTATTTTAAAATTAT ATTCTTAGCGTTTTATAAT TTTAAAATAATTCTTAGC-C3 |
| 91 | 54.4 | hairpin | TAGCGTTTTTATTTTAAAA TTATATTCTTAGCGTTTTA TAATTTTAAAATAATTCT-C3 |
| 92 | 55.2 | hairpin | GCGTTTTATTTTAAAAA TATATTCTTAGCGTTTTATA TTTTTAAAAATATTCTTA-C3 |
| 93 | 54.5 | hairpin | GCGTTTTTAATTTAAATT TATATTCTTAGCGTTTTATA AATTTAAATTAATTCTTA-C3 |
| 94 | 55.2 | hairpin | GCGTTTTTAATTTTAAAA TATATTCTTAGCGTTTTATA TTTTAAAATTAATTCTTA-C3 |
| 100 | 56.2 | hairpin | GTTTATATTTTAAAAAT TATTCTTAGCGTTTTAATTT TTAAAAATATTTCTTAGC-C3 |
| 44 | 45.0 | Non-ligated dumbbell | (amino)- TAAAATAATTCTTAGCGTT TTTATTTTAAAATTATAT TCTTAGCGTTTTATAATTT-p |
| 44 | 42 | Non-ligated dumbbell | TAAAATAATTCTTAGCGTT TTTATTTTAAAATTATATT CTTAGCGTTTTATAATTT-C3 |

Example 3

Polymerase Inhibition

Studies are done to measure the inhibitory activity of aptamers described herein as a function of temperature. Polymerase activity of Taq polymerase in the presence of aptamers is assayed by a method described in the art (Nikiforov T., *Analytical Biochemistry*, 412: 229-236 (2011) with the following modification. Because the aptamers of the present invention inhibit Taq polymerase activity above ambient temperature, the structure of the hairpin substrate is modified to increase its Tm. Hairpin substrate (SEQ ID NO: 6)
TTTTTTTGCAGGTGACAGGCGCGAAGCGCCTGTCACCXGC, wherein X denotes a fluorescein dT residue is used in the assay. To a solution of 150 nM of the hairpin substrate in 50 mM Tris-HCl, 50 mM NaCl, 5 mM MgCl$_2$, and Taq polymerase, 2 μL of 2 mM dATP is added, and the FAM signal is monitored while the reaction mixture is heated from 25° C. to 74° C. using the standard dissociation curve program (Mx3005P, Agilent). The assays measure the reversible inhibition activity of the aptamers whereby polymerase activity is regained upon heating of the reaction mixture. The temperature at which inhibition is lost depends on the sequence and structure of the aptamer.

Example 4

Hot Start Activity

To test the ability of aptamers designed as described herein to reduce non-specific product generation in a PCR reaction, a human genomic biplex PCR amplification assay was performed in which two regions of the beta-globin gene were detected followed by post-PCR melt curve analysis using Eva-Green. The two primer pairs had the sequences: AAAAGGCATTCCTGAAGCTGACAGCATTC (SEQ ID NO:7, forward primer 1) and GAGAGAGTAGCGCGAGCACAGCTA (SEQ ID NO:8, reverse primer 1); and AAAACCTGCCTTCTGCGTGAGATTCT (SEQ ID NO:9, forward primer 2) and CTGTACGAAAAGACCACAGGGCCCAT (SEQ ID NO:10, reverse primer 2). The PCR master mix, prepared at room temperature, contained 100 μM dNTPs, 5 mM MgCl$_2$, 25 mM HEPES, pH 8.5, X1 EvaGreen® (1× concentration), human genomic DNA (1000 copies/reaction), 0.30% Tween 20, and 1 mg/mL BSA. 4 u Taq DNA polymerase (GMP Taq, Roche Diagnostics) was added to each reaction from a 0.25 u/μL preparation. An aptamer comprising CAAAATAAT-TCTTAGCGTTTTTATTTTGCAATTATATTCT-TAGCGTTTTATAATT G-C3 (SEQ ID NO:106) was added to selected reactions at a concentration of 200 nM. The reactions were initiated by the addition of Taq or Taq plus aptamer. Where aptamer was included in the reaction, the Taq and aptamer were premixed at room temperature just prior to addition to the PCR master mix. The Stratagene Mx3005P 96 well-plate system (Agilent Technologies) was used to run and analyze the PCR reactions. Cycling conditions were as follows: 95° C. for 100 s, 45 cycles of 95° C. for 8 s and 68° C. for 30 s, then 95° C. for 10 s, 60° C. for 30 s, concluding with melt curve analysis at 60° C. to 95° C. over a 20 min period.

Figure 4A:
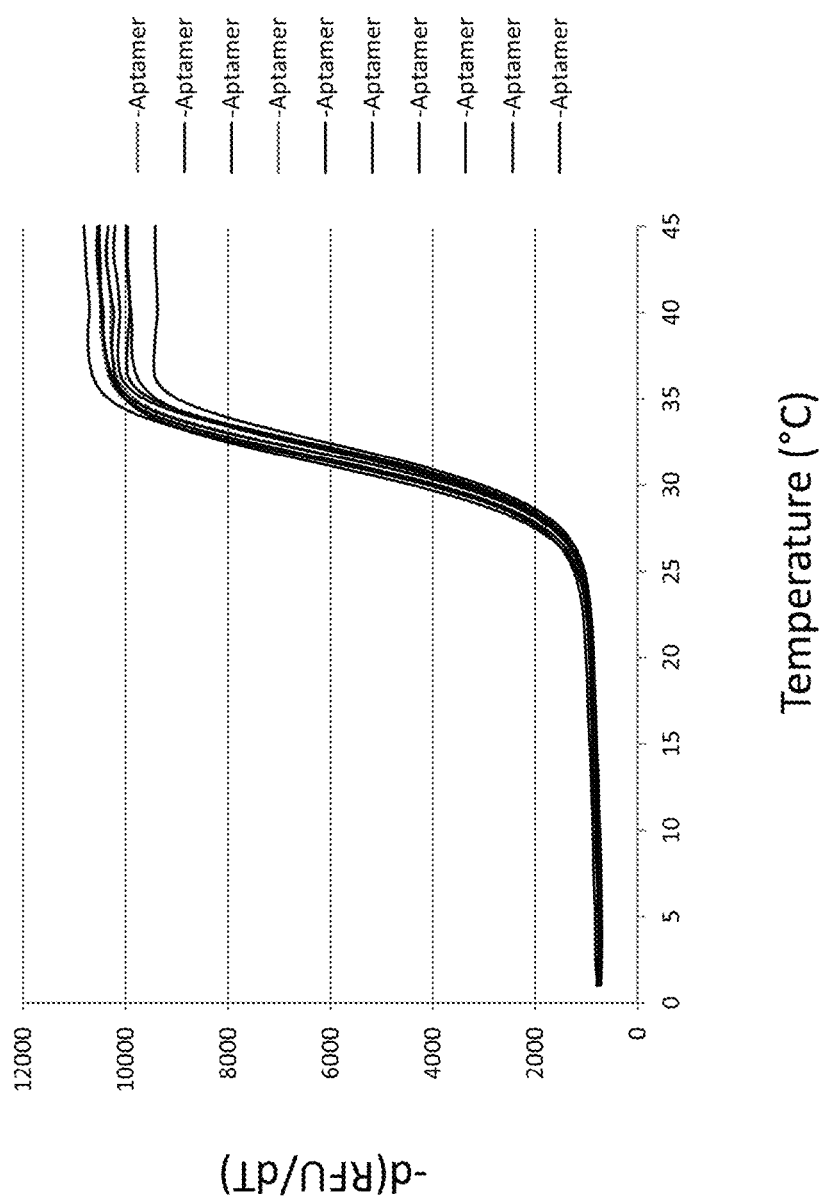
FIGS. 4A and 4B illustrate results of real time PCR reactions (Example 4) for the detection of 2 target sequences in genomic DNA. Reactions were run in the absence (FIG. 4A) and presence (FIG. 4B) of aptamers according to the present disclosure. The increase in fluorescence signifies the generation of the PCR products.
Figure 4B:
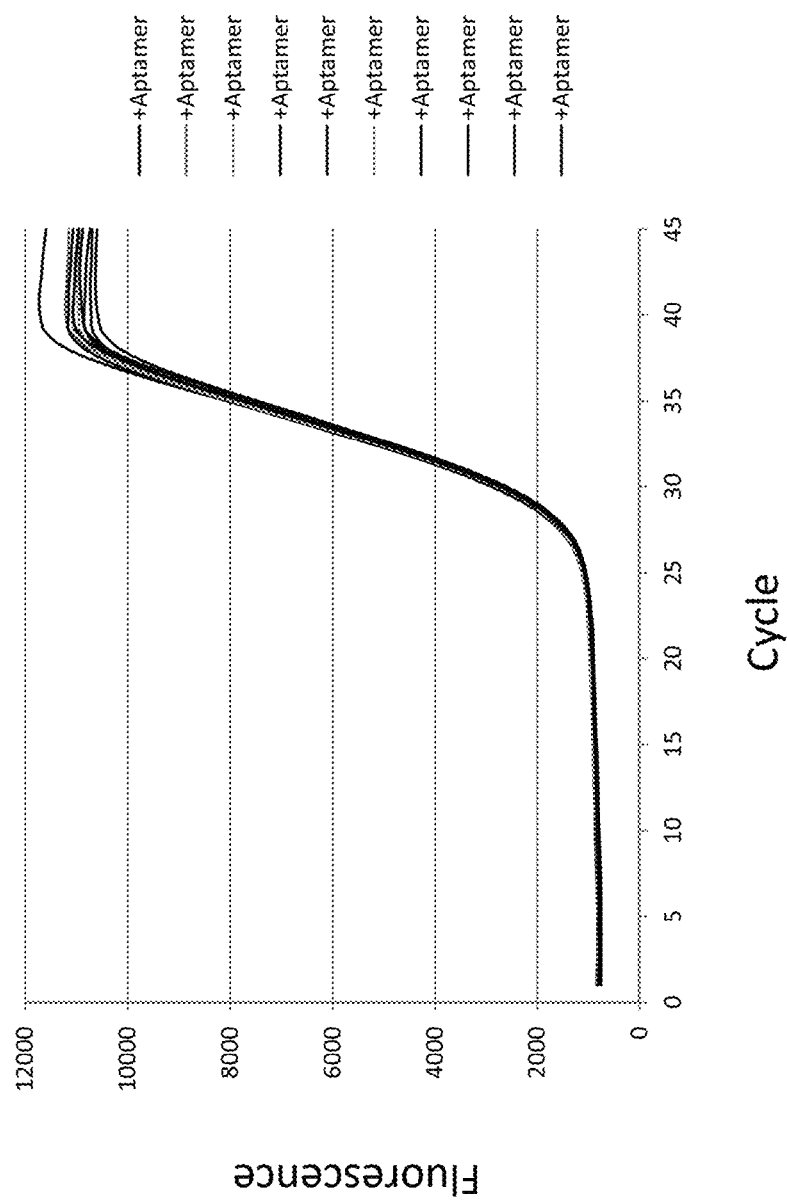
Figure 5A:
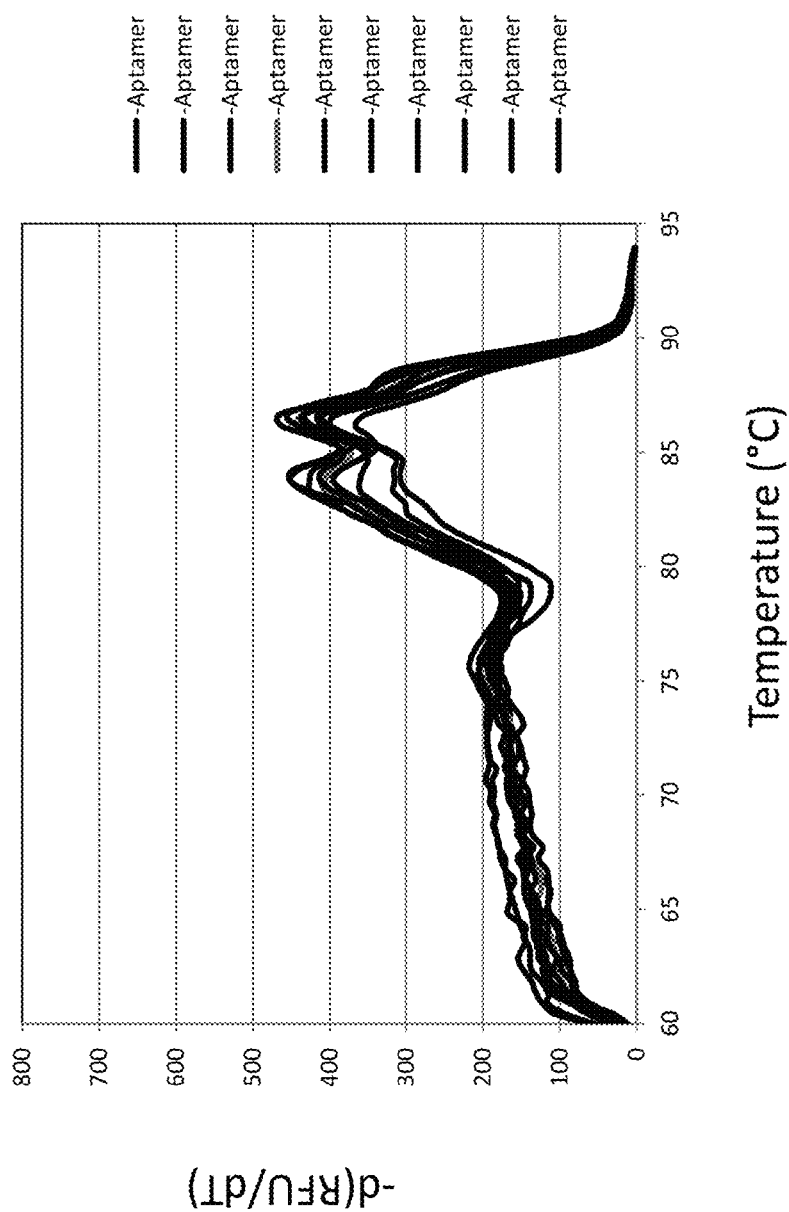
FIGS. 5A and 5B illustrate post-PCR melt curve analysis (Example 4) of real time PCR reactions shown in FIGS. 4A and 4B. Melt curve analysis of PCR products generated in the absence (FIG. 5A) and presence (FIG. 5B) shows that the presence of aptamer according to the present disclosure results in the generation of greater quantities of the target amplicons and lower quantities of non-specific products.
Figure 5B:
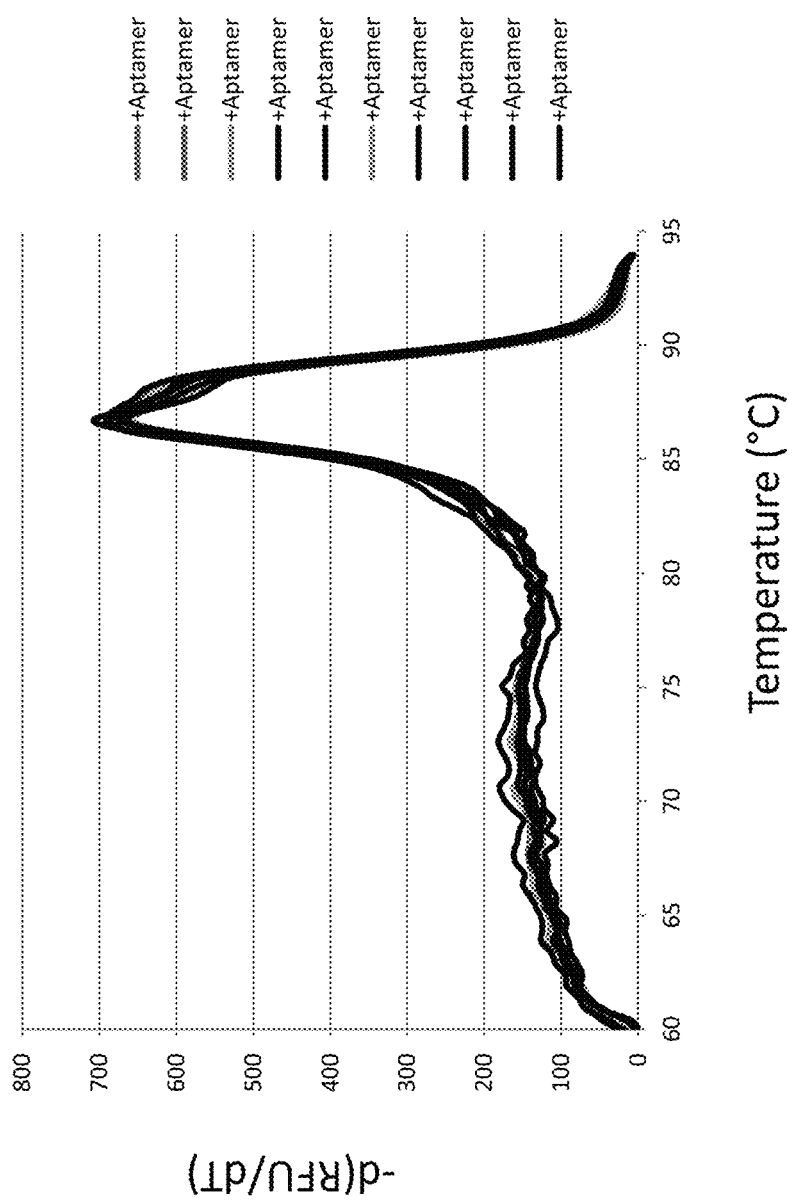

Results in which product generation measured by an increase in fluorescence vs. cycle number (FIGS. 4A and 4B) show that presence of the aptamer (FIG. 4B) resulted in higher product generation compared to absence of the aptamer (FIG. 4A). Melt curve analysis (FIGS. 5A and 5B) showed that the two specific bands corresponding to the beta-globin amplicons were detected in reactions both with and without aptamer but were not detected in reactions lacking Taq polymerase. Moreover, FIGS. 5A and 5B demonstrate a significant decrease in the generation of non-specific products in reactions containing Taq polymerase and aptamer as compared to reactions run in the absence of aptamer. The data show that quantities of the specific beta-globulin amplicons were higher in reactions containing both Taq and the aptamer. (Lane 1: molecular weight markers; corresponding bp values are to the left and right of the gel image; Lanes 2, 3, 6, 7, 8, 9: Taq and aptamer only without PCR master mix; Lanes 4, 10, 11: PCR master mix with Taq with no aptamer; Lanes 5, 12, 13: PCR master mix with Taq and aptamer.)

Example 5

Hot Start PCR

As described herein, aptamers can reversibly inhibit polymerase activity at temperatures below the optimal reaction temperature for the polymerase. Studies were done to evaluate the effects of varying aptamer:Taq (*T. aquaticus* DNA polymerase) ratios using the Xpert® *C. difficile*/Epi Assay (Cepheid), and to determine an optimal aptamer:Taq ratio with respect to target product and non-specific product generation. The aptamer used in the present example is the aptamer described herein as SEQ ID NO:106 (CAAAATAATTCTTAGCGTTTTTATTTTGCAATTAT-ATTCTTAGCGTTTTATAAT TG-C3), modified at its 3' end with a propanediol spacer CPG as described in Example 1.

Live *C. difficile* cells at 3 concentrations (275, 92, or 23 CFU/test) in a human stool background matrix were used in the assay. The experiment was run in open cartridges on the GeneXpert® instrument with all wet master mixes prepared on the day of the experiment. 48 units of Taq polymerase was used in each reaction and were run in parallel with an AptaTaq® control (Roche Diagnostics). All solutions of Aptamer:Taq were stored in 10% glycerol. Aptamer:Taq ratios of 2.5:1, 5:1, 10:1 and 15:1 were tested. Eight replicates were run for each condition. At the end of the GeneXpert® runs, amplicon was collected from the PCR tubes of the cartridges and evaluated in an Agilent DNA 1000 chip via the 2100 Agilent Bioanalyzer (Agilent Technologies). Only the 1× LoD (equivalent to 92 CFU/test) samples were selected to be evaluated in duplicates in the Agilent system.

Amplicon lengths for the targets of interest are as follow: 81 bp for toxin B (tcdB), 91 bp for tcdC deletion nt 117, 133 bp for SPC (sample-processing control) and 143 bp for binary toxin (cdt). Non-specific bands at 210 bp were observed in all reaction mixtures tested but were the faintest for the 15:1 Aptamer:Taq ratio. The non-specific bands at 210 and 400 bp were the most prominent for the 2.5:1 Aptamer:Taq ratio (data not shown).

Furthermore, the binary toxin end points increased as the amount of non-specific binding decreased (data not shown). The lowest binary toxin end points were observed with the 2.5:1 Aptamer:Taq ratio. The highest binary toxin end points were observed with the 15:1 Aptamer:Taq ratio. This suggests that more of the target binary toxin product was made when non-specific amplification was limited. The results of this study suggest that an Aptamer:Taq ratio of 15:1 for the aptamer comprising SEQ ID NO:106 is optimal for hot start PCR methods using *T. aquaticus* DNA polymerase.

It is claimed:

1. A dumbbell aptamer comprising
a single oligonucleotide in a folded configuration, the single oligonucleotide comprising
nucleotides of SEQ ID NO:1, or a variant thereof, covalently linked to
nucleotides of SEQ ID NO:3, or a variant thereof, covalently linked to
nucleotides of SEQ ID NO:2, or a variant thereof, covalently linked to
nucleotides of SEQ ID NO:3, or the variant thereof;
in the folded configuration the single oligonucleotide comprises
a nucleotide stem and two nucleotide loops,
wherein the nucleotide stem comprises
the nucleotides of SEQ ID NO:1, or the variant thereof,
hybridized to
the nucleotides of SEQ ID NO:2, or the variant thereof,
wherein the nucleotides of
SEQ ID NO:1, or the variant thereof, or
SEQ ID NO:2, or the variant thereof,
are split into
a 5' portion and
a 3' portion
due to a lack of a covalent bond between adjacent nucleotides of
SEQ ID NO:1 or the variant thereof, or
SEQ ID NO:2, or the variant thereof,
the lack of the covalent bond defining
a 5' terminus and
a 3' terminus
of the dumbbell aptamer that are positioned adjacent to one another within the nucleotide stem of the single oligonucleotide in the folded configuration,
wherein:
the variant of SEQ ID NO: 1 has only 1 to 4 nucleotide substitutions in SEQ ID NO:1;
the variant of SEQ ID NO:2 has only 1 to 4 nucleotide substitutions in SEQ ID NO:2;
the variants of SEQ ID NO: 1 and SEQ ID NO:2 are equal in length to each other, and are
100% complementary to each other along their entire length; and
each of the two nucleotide loops of the single oligonucleotide, in the folded configuration, individually comprise
SEQ ID NO:3, or variants thereof,
the variants of SEQ ID NO:3 having only 1 or 2 nucleotide substitutions in SEQ ID NO: 3.

2. The dumbbell aptamer of claim 1, wherein
the nucleotides of SEQ ID NO:1, or the variant thereof, are
split into
the 5' portion and
the 3' portion,
defining
the 5' terminus and
the 3' terminus
within SEQ ID NO:1 or the variant thereof.

3. The dumbbell aptamer of claim 1, wherein
the nucleotides of SEQ ID NO:2, or the variant thereof, are
split into
the 5' portion and
the 3' portion,
defining
the 5' terminus and
the 3' terminus
within SEQ ID NO:2 or the variant thereof.

4. The dumbbell aptamer of claim 2, wherein the nucleotides of SEQ ID NO: 1 lack said covalent bond between nucleotides 8 and 9.

5. The dumbbell aptamer of claim 3, wherein the nucleotides of SEQ ID NO: 2 lack said covalent bond between nucleotides 8 and 9.

6. The dumbbell aptamer of claim 2, wherein:
the 5' terminus, is phosphorylated;
the 3' terminus is linked to a 3' capping moiety;
the 5' terminus, is linked to a 5' capping moiety; or
the 3' terminus is linked to the 3' capping moiety and the 5' terminus, is linked to the 5' capping moiety.

7. The dumbbell aptamer of claim 6, wherein
the 3' capping moiety is
a propanediol spacer (C3) or
a phosphate.

8. The dumbbell aptamer of claim 6, wherein
the 5' capping moiety is an amino group.

9. The dumbbell aptamer of claim 3, wherein:
the 5' terminus is phosphorylated;
the 3' terminus is linked to a 3' capping moiety;
the 5' terminus is linked to a 5' capping moiety; or
the 3' terminus is linked to the 3' capping moiety and the 5' terminus is linked to the 5' capping moiety.

10. The dumbbell aptamer of claim 9, wherein
the 3' capping moiety is
a propanediol spacer (C3) or
a phosphate.

11. The dumbbell aptamer of claim 9, wherein the 5' capping moiety is an amino group.

12. A composition comprising
the dumbbell aptamer according to claim 1 and
a thermostable polymerase.

13. The composition of claim 12, wherein
the molar ratio of
  the dumbbell aptamer to
  the thermostable polymerase
ranges from
  about 2:1 to
  about 15:1.

14. The composition of claim 12, wherein
the molar ratio of
  the dumbbell aptamer to
  the thermostable polymerase
is about 1:1, 2:1 or 4:1.

15. An aptamer consisting of SEQ ID NO: 110 wherein the 5' and 3' ends are ligated.

16. An aptamer comprising SEQ ID NO: 106 or a variant thereof; and
the aptamer further comprising a secondary structure comprising
  two nucleotide loops and
  a nucleotide stem;
wherein the variant of SEQ ID NO:106 comprises
  fewer than 3 nucleotide substitutions in each of the two nucleotide loops,
  fewer than 9 nucleotide substitutions in the nucleotide stem, and
  fewer than 13 nucleotide substitutions in total.

17. A method for extending a primer, the method comprising
contacting a sample which might contain a target nucleic acid with a reagent composition to generate a reaction mixture;
wherein the reagent composition comprises
  the dumbbell aptamer according to claim 1,
  a thermostable polymerase,
  a forward primer specific for the target nucleic acid,
  deoxyribonucleotide triphosphates, and
  a divalent metal cation.

18. The method of claim 17, wherein
the ratio of
  the dumbbell aptamer to
  the thermostable polymerase
ranges from about 2:1 to 15:1.

19. The dumbbell aptamer of claim 1, wherein
the single oligonucleotide is at least a 56-mer.

20. The dumbbell aptamer of claim 1, wherein
the single oligonucleotide comprises SEQ ID NO:106.

* * * * *